United States Patent
Suzuki et al.

(10) Patent No.: US 8,005,187 B2
(45) Date of Patent: Aug. 23, 2011

(54) MEDICAL DIGITAL X-RAY IMAGING APPARATUS AND MEDICAL DIGITAL X-RAY SENSOR

(75) Inventors: Masakazu Suzuki, Kyoto (JP); Hideki Yoshikawa, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 12/083,661

(22) PCT Filed: Oct. 17, 2006

(86) PCT No.: PCT/JP2006/320647
§ 371 (c)(1),
(2), (4) Date: Apr. 16, 2008

(87) PCT Pub. No.: WO2007/046372
PCT Pub. Date: Apr. 26, 2007

(65) Prior Publication Data
US 2009/0168966 A1    Jul. 2, 2009

(30) Foreign Application Priority Data

Oct. 17, 2005    (JP) .................................. 2005-301973

(51) Int. Cl.
*A61B 6/14* (2006.01)
(52) U.S. Cl. .......................................... 378/39; 378/19
(58) Field of Classification Search .............. 378/37–39, 378/19
See application file for complete search history.

(56) References Cited

U.S. PATENT DOCUMENTS

| | | | |
|---|---|---|---|
| 5,511,106 A | 4/1996 | Doebert et al. | |
| 5,677,940 A | 10/1997 | Suzuki et al. | |
| 6,118,842 A * | 9/2000 | Arai et al. | 378/39 |
| 6,289,074 B1 * | 9/2001 | Arai et al. | 378/4 |
| 6,584,171 B2 | 6/2003 | Suzuki et al. | |
| 7,054,409 B2 | 5/2006 | Ross et al. | |
| 2001/0021244 A1 | 9/2001 | Suzuki et al. | |
| 2003/0169847 A1* | 9/2003 | Karellas et al. | 378/98.3 |
| 2004/0101095 A1* | 5/2004 | Jing et al. | 378/37 |
| 2004/0125917 A1 | 7/2004 | Ross et al. | |
| 2005/0135558 A1* | 6/2005 | Claus et al. | 378/42 |

FOREIGN PATENT DOCUMENTS

| | | |
|---|---|---|
| DE | 19941668 | 3/2000 |
| DE | 101 08 385 | 9/2001 |
| EP | 0 776 124 | 5/1997 |
| FI | 974420 | 6/1998 |
| JP | H9-122118 | 5/1997 |
| JP | 10-225455 | 8/1998 |
| JP | 8-257026 | 10/1998 |
| JP | 2001-231779 | 8/2001 |
| JP | 2002-17718 | 1/2002 |
| JP | 2003-159241 | 6/2003 |
| JP | 2004-230154 | 8/2004 |

* cited by examiner

*Primary Examiner* — Hoon Song
(74) *Attorney, Agent, or Firm* — DLA Piper LLP (US)

(57) ABSTRACT

In a medical digital X-ray imaging apparatus having a plurality of imaging modes including computed tomography mode, a supporter supports an X-ray source and a digital X-ray sensor having a two-dimensional detection plane for detecting X-rays, while interposing an object between them. An image reconstructor acquires data from the digital X-ray sensor and reconstructs an image based on the acquired data. An operator selects one of a first imaging mode and a second imaging mode. The second imaging mode has an irradiation field different from the first imaging mode and has an area to be read in the digital X-ray sensor smaller than that in the first imaging mode.

10 Claims, 28 Drawing Sheets

SENSOR NEEDED
FOR CT IMAGING
← PIXEL

SENSOR NEEDED
FOR PANORAMIC
IMAGING
← PIXEL

SENSOR NEEDED
FOR CT IMAGING
WITH LIMITED
IRRADIATION FIELD

SUPERPOSITION OF IMAGES IN PANORAMIC IMAGING

SENSOR NEEDED FOR CT IMAGING

SENSOR NEEDED FOR PANORAMIC IMAGING (a)

(b)

(a)

(b)

MEDICAL DIGITAL X-RAY IMAGING APPARATUS AND MEDICAL DIGITAL X-RAY SENSOR

TECHNICAL FIELD

The invention relates to a medical X-ray imaging apparatus and a medical digital X-ray sensor for digital X-ray imaging.

BACKGROUND ART

A digital X-ray sensor having a two-dimensional detection plane is used for a medical X-ray imaging apparatus. There are various imaging modes in X-ray imaging such as computed tomography (CT) imaging, panoramic imaging (imaging of entire jaws), cephalometric imaging (head normalization photographing) and dental imaging (imaging of one or a few teeth in a small irradiation field). A digital sensor is developed to have an appropriate size and performance for each of the imaging modes. It is desirable that one X-ray imaging apparatus can be used in a plurality of modes. For example, in a digital X-ray imaging apparatus disclosed in JP-A H8-257,026/1996, an X-ray MOS sensor is used for panoramic tomography or linear tomography. Slit plates are provided for an X-ray source and for an X-ray MOS sensor, and the sizes of the openings of the slits are controlled according to an imaging mode among the panoramic tomography and linear tomography, and a range of pixels to be read in the MOS sensor is changed. An X-ray imaging apparatus disclosed in JP-A H10-225,455/1998 can change an imaging mode between computed tomography mode and panoramic tomography mode. Slit plates are provided for an X-ray source and for an X-ray MOS sensor, and the sizes of the openings of the slits are controlled according to an imaging mode among computed tomography and panoramic tomography modes.

However, in the X-ray imaging apparatus disclosed in JP-A H10-225,455/1998 for two imaging modes, a detection area in the digital X-ray sensor necessary for panoramic imaging is smaller than that for computed tomography imaging. Therefore, if the same digital X-ray sensor is used both for computed tomography imaging and for panoramic imaging, data are read out from pixel not needed to be read, so that excess data are transferred and stored, and a time therefor is wasted. Further, exposure to X-ray radiation is increased unnecessarily in proportion to the area in the two-dimensional detection plane. Therefore it is generally desirable that the digital X-ray sensor can be used efficiently for each imaging mode. It is described on the digital X-ray imaging apparatus disclosed in JP-A H8-257,026 having two imaging modes that the slits are changed according to the imaging mode, but it is not described to change an area for reading data or a time for reading data according to imaging mode in contrast to the embodiments of the invention to be explained later.

DISCLOSURE OF THE INVENTION

An object of the invention is to use a digital X-ray sensor efficiently according to imaging mode in a medical X-ray imaging apparatus having a plurality of imaging modes.

Another object of the invention is to provide a digital X-ray sensor to be used efficiently according to imaging mode.

In this description, "to reconstruct an image" denotes generally to construct an image such as a computed tomography image or a panoramic image derived from X-ray image data read from a digital X-ray sensor. Further, "cross tomography" is used to represent a radiography called "transverse tomography".

A medical digital X-ray imaging apparatus according to the invention has a plurality of imaging modes including computed tomography mode. The apparatus has an X-ray source for generating X-rays, a digital X-ray sensor having a two-dimensional detection plane for detecting the X-rays, a supporter which supports the X-ray source and the digital X-ray sensor while interposing an object between them, an image reconstructor which acquires data from the digital X-ray sensor and reconstructs an image based on the acquired data, and a mode selector for selecting one of a first imaging mode and a second imaging mode. An irradiation field in the second imaging mode is different from that in the first imaging mode and an area in the digital X-ray sensor from which image data are read is shorter in the second imaging mode than that in the first imaging mode.

In the digital X-ray sensor in the medical digital X-ray imaging apparatus, preferably, a time for acquiring the image data in an imaging area of the object in the second imaging mode is shorter than that in the first imaging mode.

The medical digital X-ray imaging apparatus preferably has a combiner which combines signals of adjacent imaging elements to be dealt as a pixel.

In the medical digital X-ray imaging apparatus, the first imaging mode is, for example, computed tomography mode or simple X-ray imaging, and the second imaging mode is, for example, one of panoramic imaging mode, a cephalometric imaging mode and dental imaging mode. Alternatively, the first imaging mode is cephalometric imaging mode or simple X-ray imaging, and the second imaging mode is one of panoramic imaging mode, cross tomography imaging mode and dental imaging mode. In the apparatus, preferably, frame late can be changed during imaging in the second imaging mode, for example, based on a predetermined change pattern or a position of the supporter during imaging.

A medical digital X-ray sensor according to the invention has a two-dimensional detection plane for detecting X-rays transmitting an object in a plurality of imaging modes including computed tomography scanning. An area in the two-dimensional detection plane from which image data are read is changed according to selection among first and second imaging modes, an irradiation field in the second imaging mode is different from that in the first imaging mode, and an area in the two-dimensional detection plane from which the image data are read in the second imaging mode is smaller than that in the first imaging mode.

ADVANTAGES OF THE INVENTION

It is an advantage of the invention that an area from which image data in the digital X-ray sensor are read is changed for each imaging mode so that image data of an optimum data capacity can be acquired in an optimum time.

It is another advantage of the invention that the image data can be acquired without excess time for each imaging mode by optimizing data acquisition time.

It is a still another advantage of the invention that image data capacity can be decreased by combining signals of adjacent imaging elements to be dealt as a pixel.

It is a further advantage of the invention that the frame rate can be changed during imaging so that the amount of image data is controlled to become just enough if necessary.

It is a still further advantage of the invention that an optimum data capacity and an optimum data acquisition time can be realized for various imaging modes such as computed tomography scanning mode, panoramic imaging mode, cephalometric imaging mode, cross tomography imaging mode and dental imaging mode, so that a dose of exposure to radiation of a patient can be decreased and diagnosis efficiency can be improved.

MODE FOR CARRYING OUT THE INVENTION

Embodiments of the invention are explained below with reference to the drawings appended herewith.

Figure 1:
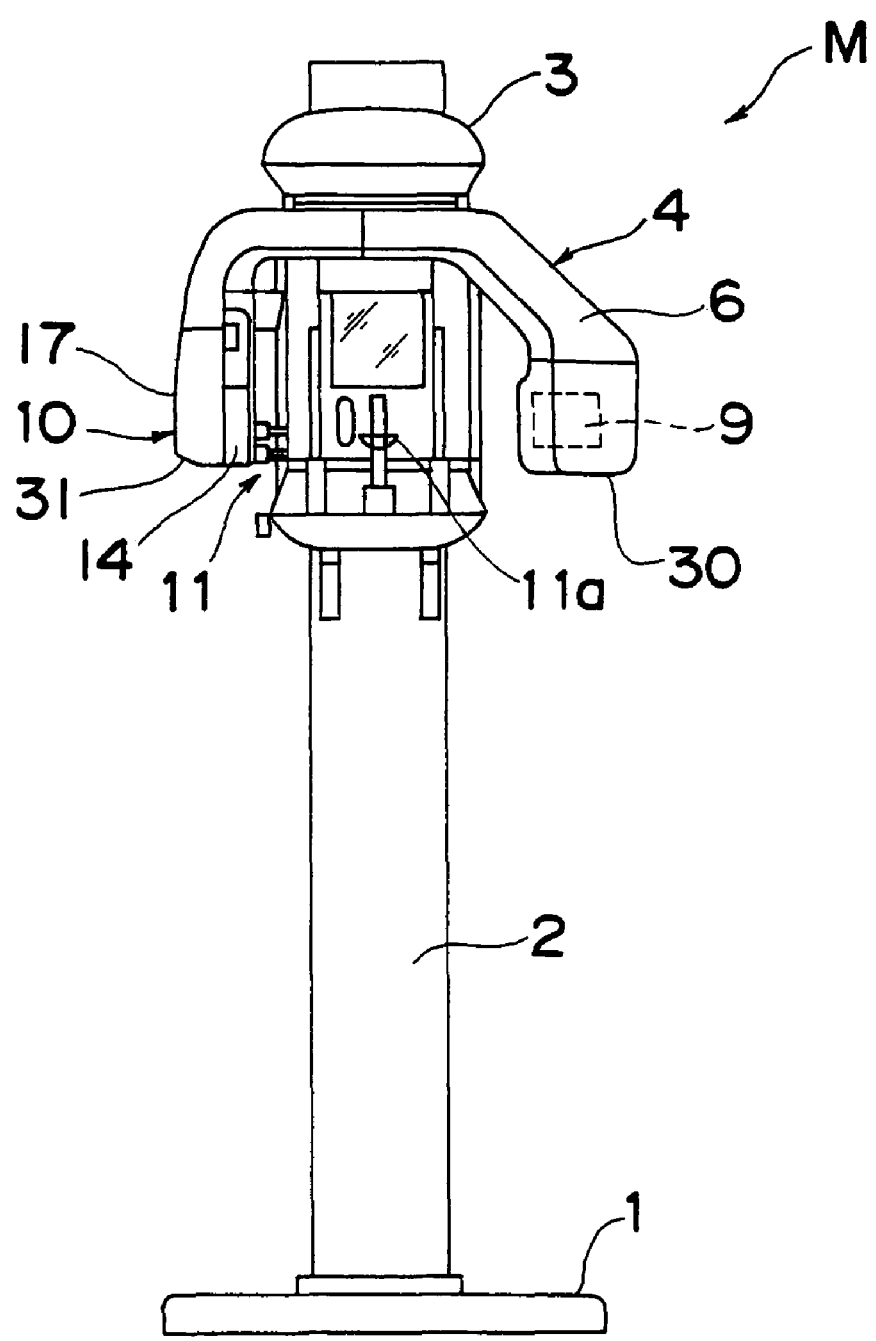
FIG. 1 is a diagram of an X-ray imaging apparatus.

FIG. 1 shows a digital X-ray radiography apparatus such as a dental X-ray radiography apparatus according to an embodiment of the invention. Though the embodiments are explained below with reference to examples of the dental X-ray radiography apparatus, the invention is not limited to dentistry, but can be used generally for medical uses.

In FIG. 1, X-rays generated by an X-ray source transmits an object and are detected by a digital X-ray sensor having a detection plane. By limiting an imaging area in the detection plane to a necessary area, a dose of radiations exposed to a patient can be reduced to the lowest limit. Further, reconstruction of image data is performed on a selected range in the imaging area. For example, an irradiation field of X-rays generated by the X-ray source can be changed by adjusting a slit for the X-ray source, and data necessary for image reconstruction can be read out selectively according to the irradiation field from imaging elements in the digital X-ray sensor. Thus, data processing time can be shortened, and data capacity can be optimized. Further, the X-ray imaging apparatus has a plurality of imaging modes. It can be used for X-ray computed tomography (CT) imaging, and it can also be used for panoramic imaging, cephalometric imaging, cross tomography imaging and dental imaging. Otherwise this dental X-ray radiography apparatus is similar to a prior art X-ray CT scanner.

The X-ray radiography apparatus shown in FIG. 1 is explained in detail. It has a base 1 provided on a floor, a support 2 extending upward from the base 1, and a frame 11 to be moved up and down. The frame 11 is mounted to the support 2 so as to be moved up and down vertically with a motor (not shown) for controlling the up and down movement. A horizontal frame 3 extends from the top of the frame 11 forward horizontally. Another frame extends from the bottom thereof forward horizontally, and a chin rest 11a is mounted on the other frame so that a position thereof can be controlled. A patient as an object stands on the base 11, and put his or her chin on the chin rest 11a. Thus, a region to be imaged is positioned as an imaging region. Alternatively, a patient's chair (not shown) is mounted on the base 1 or on a different base (not shown). A patient sits on the chair, and the chair is moved for positioning a portion of the object to be imaged at an imaging region. The chair is an example of a device for holding an object.

Figure 2:
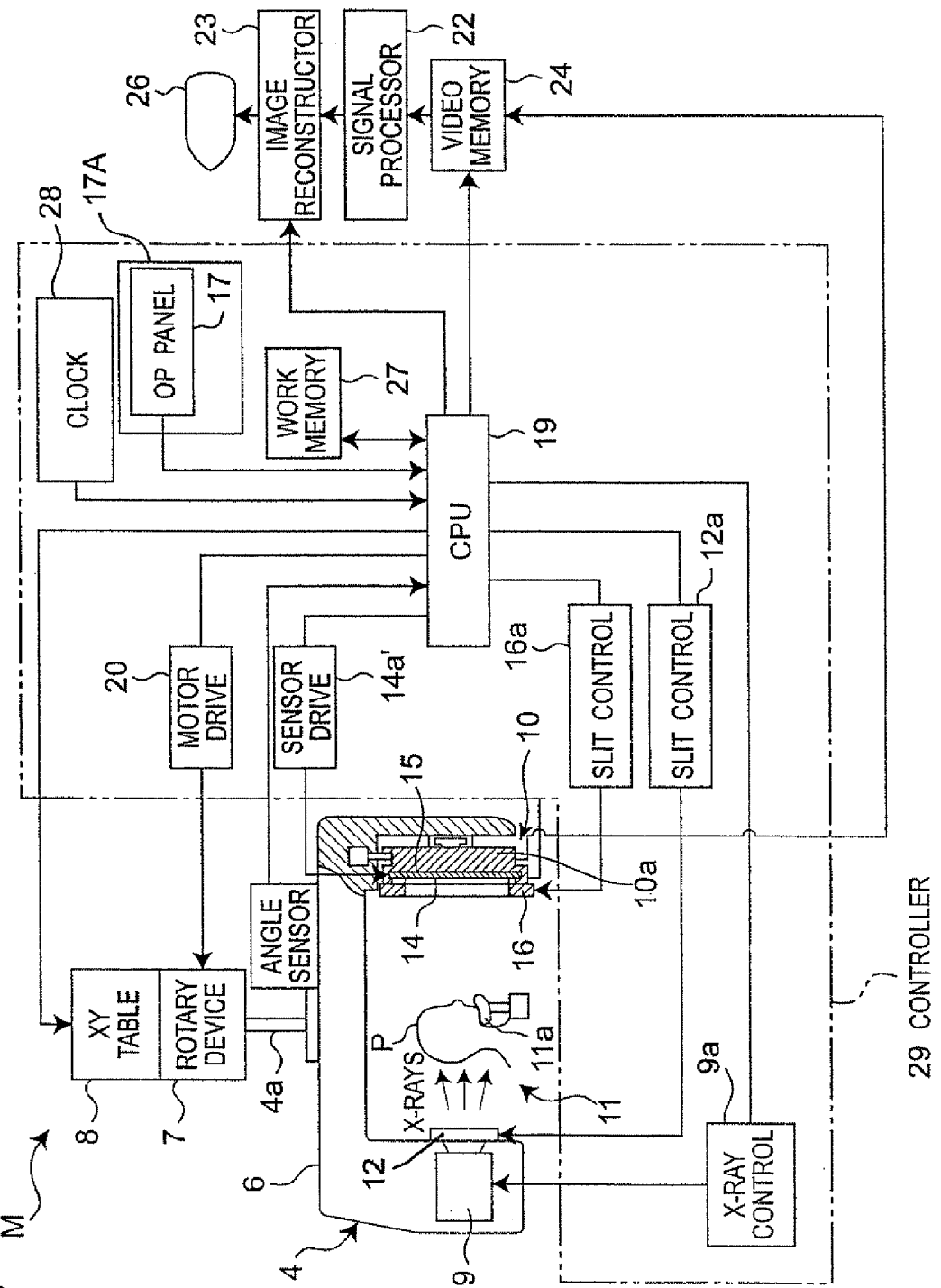
FIG. 2 is a block diagram of a control system of the X-ray imaging apparatus.

FIG. 2 shows a general block diagram on a control system of the X-ray radiography apparatus shown in FIG. 1. The structure of the X-ray radiography apparatus is explained further with reference to FIGS. 1 and 2. A horizontal movement mechanism is provided in the horizontal frame 3, and it includes an XY table 8 movable in two dimensions in back-and-forth and right-and-left directions. The horizontal movement mechanism is used for panoramic imaging. The XY table 8 includes a rotary device 7 therein. The rotary device 7 such as a rotary motor supports a rotary shaft 4a rotatably, which is connected to a central portion 6 of a rotary arm 4. The rotary device 7 such as a rotary motor is rotated according to a motor drive signal 20. Alternatively, the rotary device 7 is provided in the rotary arm 4 so that the XY table 8 supports the rotary shaft 4a and rotates the rotary arm 4 around the rotary shaft 4a. Alternatively, in the case of the X-ray imaging apparatus having the patient's chair, an XY table for moving the chair itself is provided in the base 1, and the rotary device 7 is provided in the horizontal frame 3 or in the rotary arm 4. Alternatively, the rotary arm 4 is supported rotatably on the base 1, without suspended from the horizontal frame 3. In this case, the XY table 8 and the rotary device 3 are provided appropriately in the base 1 or in the rotary arm 4.

Figure 3:
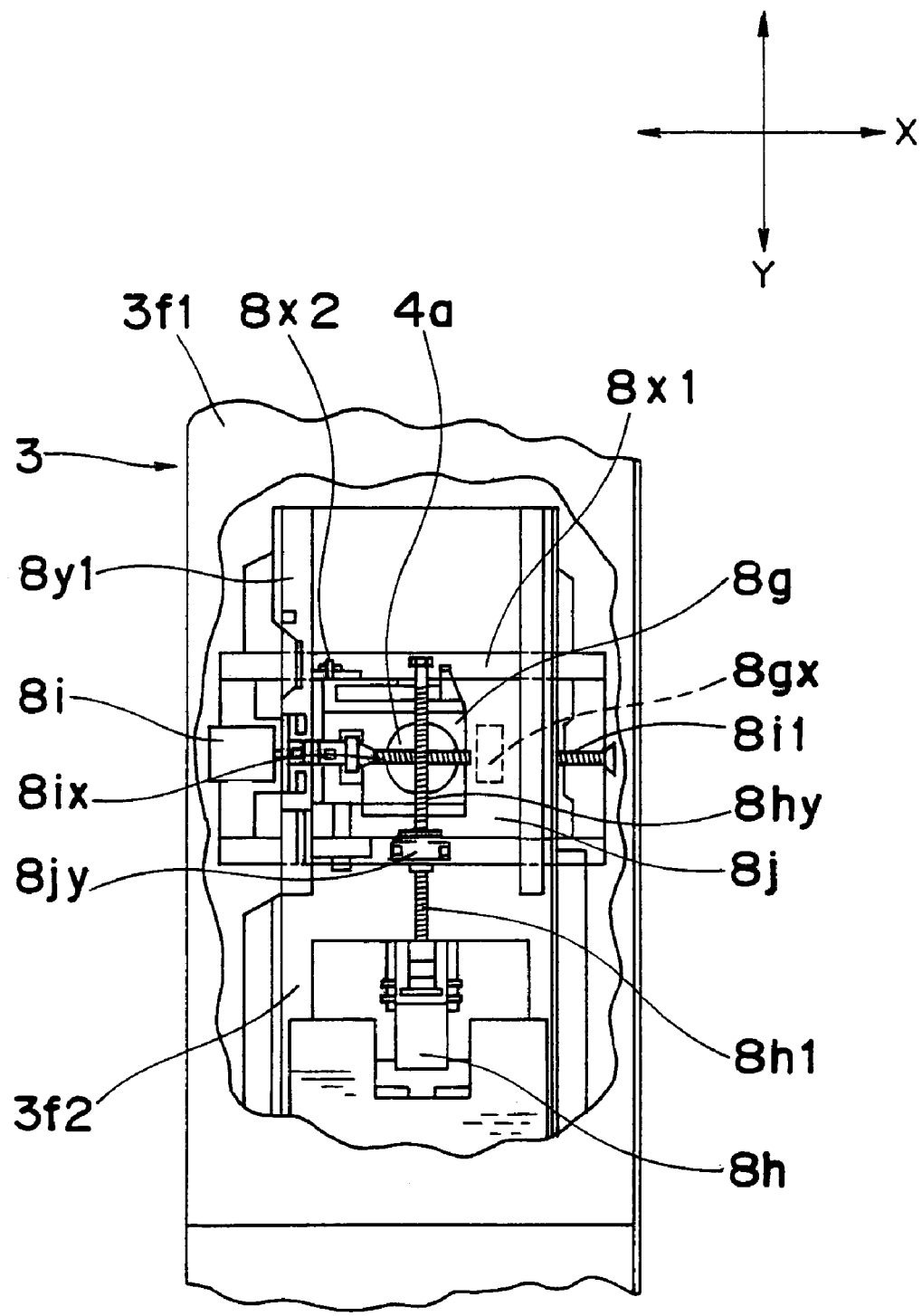
FIG. 3 is a partial sectional top view of an X-Y table.

FIG. 3 is a partial sectional top view of the horizontal frame 3 and shows an example of the XY table 8 provided in the horizontal frame 3. The inner structure at the upper side of the horizontal frame 3 holding the rotary arm 4 below is explained with reference to FIG. 3. The XY table 8 has an X table 8g and a Y table 8j. A motor 8h for control along Y axis is fixed to the horizontal frame 3 and rotates a rotary shaft 8h1 connected to the motor 8h to move the Y table 8j in parallel to Y axis. Further, a motor 8i for control along X axis is fixed to the Y table 8j and rotates a rotary shaft 8i1 connected to the motor 8i to move the X table 8g in parallel to X axis.

The structure of the horizontal frame 3 is explained further. The horizontal frame 3 has a housing 3f1 and a beam 3f2 to which the housing 3f1 is fixed, and the Y-axis control motor 3f1 is fixed to the beam 3f2. The motor 8h has a shaft 8hy as a screwed shaft for driving in Y axis. When the shaft 8hy is driven for rotation, a component 8jy screwed inside and fixed to the Y table 8j is shifted in Y direction shown in FIG. 3. The Y table 8j has a wheel 8y2 (refer to FIG. 4), and the beam 3f2 has a rail 8y1 for guiding the wheel 8y2. Therefore, when the motor 8h is rotated, the Y table 8j is moved smoothly along the rail 8y1.

On the other hand, the motor 8i for control along X axis is fixed to the Y table 8j, and it has a drive shaft 8ix as a screw shaft. When the shaft 8ix is rotated, a component 8gx fixed to the X table 8g and screwed inside is shifted in X direction shown in FIG. 3. The X table 8g has a wheel 8x2, and a rail 8x1 for guiding the wheel 8x2 is mounted on the Y table 8j. Therefore, when the motor 8i is rotated, the X table 8g is moved smoothly along the rail 8x1.

Figure 4:
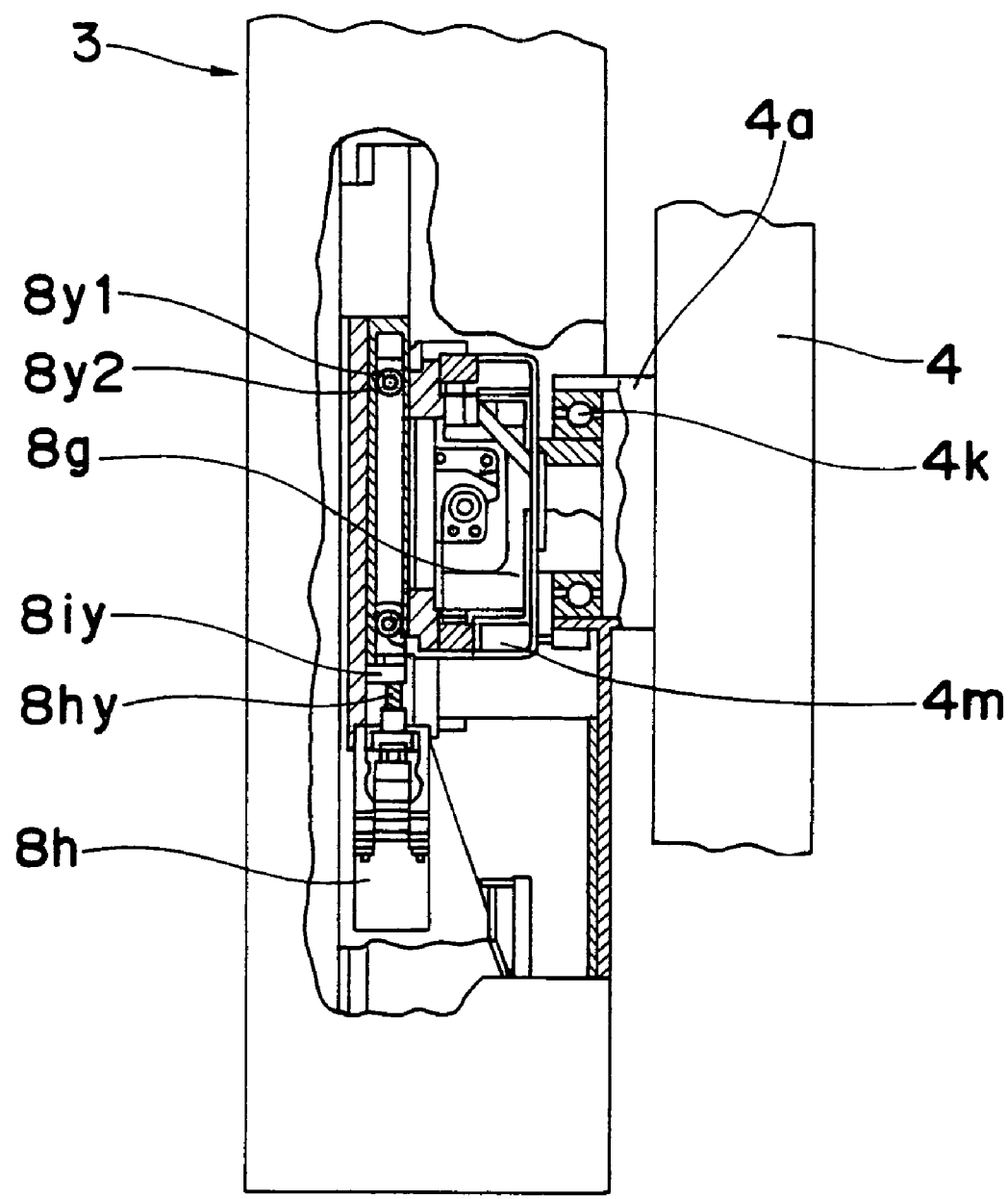
FIG. 4 is a partial sectional view of a connection between a top of a horizontal frame and a rotary arm (supporter).

FIG. 4 is a partial sectional view for explaining a connection between a top of the horizontal frame 3 and the rotary arm 4. The rotary arm 4 is an example of a supporter which supports the X-ray source 9 and the digital X-ray sensor 14 opposing to each other while interposing an object between them. The rotary arm 4 is connected rotatably with a ball bearing 4k to the rotary shaft 4a. When a motor 4m fixed to the X table 8g is driven for rotation, the rotary shaft 4 is rotated around the rotary shaft 4a. The motor 4m is an example of the rotary device 7. Alternatively, as to the rotary arm 4, a circular structure has an X-ray source in a part of the circle and a digital X-ray sensor in a different part thereof. In this case, the X-ray source and the X-ray sensor oppose to each other and interpose an object between them. Therefore, this is also an example of the rotary arm 4. In this sense, a cylindrical gantry used in a medical X-ray CT scanner is also an example of the rotary arm 4.

The motor 4m for controlling the rotation is fixed to the X table 8g, and the motor 4m gives a rotation force to the rotary shaft 4a. Because the ball bearing 4k is interposed between the X table 8g and the rotary shaft 4a, the motor 4m gives the rotation force to the shaft 4a with a very small friction resistance.

Figure 5:
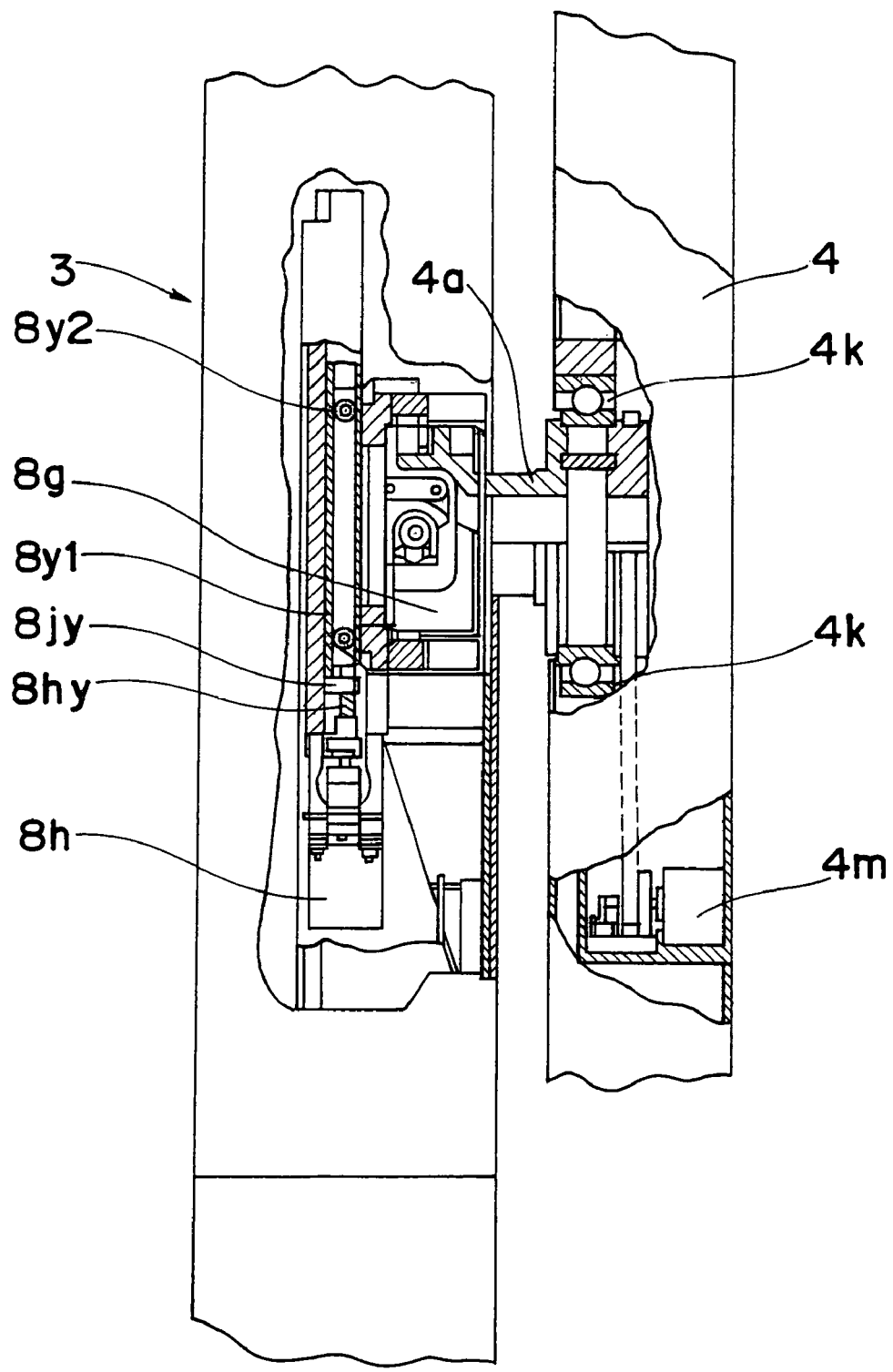
FIG. 5 is a partial sectional view of a connection between a top of the horizontal frame and the rotary arm (supporter) in a different embodiment.

In an embodiment shown in FIG. 5, in contrast to the embodiment shown in FIG. 4, the motor 4m for rotation control is mounted in the rotary arm (supporter) 4, and the rotation force is given to the rotary shaft 4a with a pulley and a belt. Otherwise the structure shown in FIG. 5 is the same as that shown in FIG. 4.

As to the XY table 8, refer to JP-A H11-204123/1999, JP-A H11-104124/1999 and JP-A H11-194125/1999 of the applicant.

The rotary arm (supporter) 4 has a first attachment 30 extending vertically at an end thereof and a second attachment 31 extending vertically at the other end thereof. The first attachment 30 has the X-ray source 9 and a primary slit mechanism 12. The primary slit mechanism 12 is mounted to the X-ray source 8 near and before the X-ray source 9. In the second attachment 31, an X-ray imaging unit 10 is mounted while opposing to the X-ray source 9. The X-ray imaging unit 10 has a cassette holder 10a, which is used to set a cassette 15 of a digital X-ray sensor 14 which detects X-rays irradiated by the X-ray source 9. The digital X-ray sensor 14 is, for example, an X-ray metal-oxide semiconductor (MOS) sensor. In the X-ray MOS sensor, MOS sensors for image detection are arranged behind a scintillator layer for converting X-rays to visible light, and the visible light is subjected to photoelectric conversion. The electrical signal is converted to a digital signal. An optical fiber layer is provided usually between the scintillator layer and the MOS sensors. Generally, any sensor is used as the digital X-ray sensor 14 if a plurality of images can be converted to signals in the unit of frame in a time. For example, a charge-coupled detector (CCD) sensor may be used. Further, the X-ray imaging unit 10 has the secondary slit mechanism 16 provided near and before the digital X-ray sensor 14. A focus of the X-ray source 9 is opposed to the two-dimensional detection plane of the X-ray digital sensor, while interposing an object between them.

The irradiation field can be changed with the primary and secondary slit mechanisms 12 and 16. A structure shown in FIGS. 14 to 18B may be used as the primary slit mechanism 12. An opening (irradiation field) of a slit may be defined, for example, by a pair of width shielding members and a pair of height shielding members. The width and the height of the opening may be controlled by moving the shielding members to set the distances between them. In this case, if each of the shielding members is controlled independently of each other, any irradiation field which can be set by the primary slit mechanism shown in FIGS. 14 to 18B can be formed when needed.

The axial direction of the rotary shaft 4a of the rotary arm (supporter) 4 is set vertically relative to the floor in the first embodiment. However, the axial direction of the rotary shaft 4a can be set freely, for example horizontally or at a desired angle. When the axial direction is set horizontally relative to the floor, a bed on which a patient lies may be used as a device for holding a patient.

The control system of the X-ray imaging apparatus shown in FIG. 1 is explained with reference to FIG. 2. A controller 29 has a central processing unit (CPU) 19 which controls the entire system. The CPU 19 is operated based on clock signals generated by a clock generator 28 and uses a work memory 27. An operator uses an operation panel 17 provided in an X-ray imaging unit 10 in order to select an imaging mode such as CT imaging or panoramic imaging and to set irradiation field, resolution and the like. These settings will be explained later. Alternatively, an operation panel 17 may be provided outside an X-ray protection room or the like. The CPU 19 receives operator's instructions from an operation unit 17A including the operation panel 17 and evokes programs for the various control and data processing based on the instructions to control the X-ray imaging. The rotation angle of the rotary arm (supporter) 4 is detected with an angle sensor. The CPU 19 makes a slit controller 12a to drive the primary slit mechanism 12 at the side of the X-ray source 9 and makes a slit controller 16a to drive the secondary slit mechanism 16 at the side of the digital X-ray sensor 14 based on the instructions. Further, it makes an X-ray controller 9a to control the X-ray source 9. As an operator selects an imaging mode with the operation unit 17A, the irradiation field of the X-ray source 9 and that of the digital X-ray sensor 14 are changed. Further, the digital X-ray sensor 14 is controlled by a sensor control signal generator 14a' to read out X-ray image data. A sensor control circuit for the digital X-ray sensor may be provided in the controller 29 or in the X-ray imaging unit 110. The rotary arm (supporter) 4 is rotated according the motor drive signal 20 to move the X-ray source 9 and the digital X-ray sensor 14, while the X-ray source 9 irradiates an X-ray beam to an object in the irradiation field set as mentioned above and the X-ray transmitting the object is detected with the digital X-ray sensor 14 to acquire X-ray image data. The X-ray image data acquired with the digital X-ray sensor is stored in a video memory 24. The image reconstructor program (an image reconstructor 23) reconstructs an image based on the X-ray image data acquired on the pixels and displays a reconstructed image with a display device 26.

Figure 6:
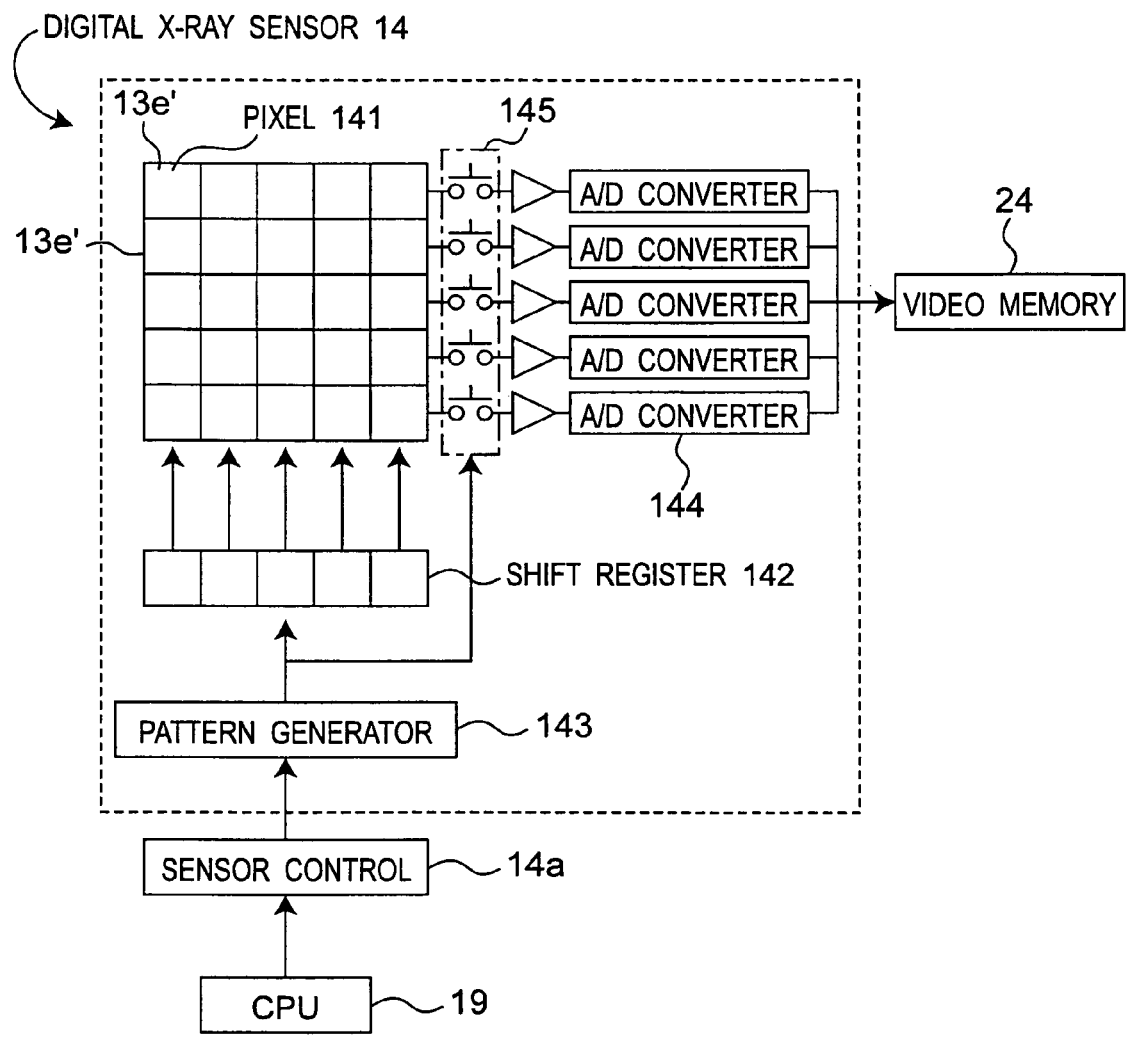
FIG. 6 is a diagram of an example of read out of image data from a digital X-ray sensor.

An example of reading out image data is explained with reference to FIG. 6. A sensor control signal 14a as one of control signals is sent by the CPU 19 to the digital X-ray sensor 14 according to imaging mode. Based on the sensor control signal 14a a pattern generator 143 selects and controls elements to be operated in a shift register 142. Thus the shift register 142 designates a row of pixels from which image data are read. The image data are read as analog signals from the row of pixels selected among the pixels which detect X-ray image data. The image data as analog signals are converted to digital signals of the image data by analog-to-digital converters 144 and are sent to a video memory 24. As mentioned above, based on the image data stored in the video memory 24, the image reconstructor 23 forms a reconstruction image, and the display device 26 displays it. As to the designation of a column of pixels 14, for example, a switching element 145 to be selected by the pattern generator 143 is provided at the output side of each row, and one of the switching elements in correspondence to a column to be read is selected. The two-dimensional detection plane 13e of the digital X-ray sensor 14 is made of a plurality of imaging elements 13e' adjacent to each other. A pixel in the pixels 141 corresponds to each of imaging elements 13e' basically. However, in a case such as binning process to be explained later, X-ray image data of a plurality of adjacent imaging elements may be dealt as one pixel.

Figure 7:
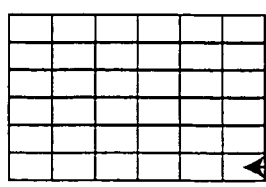
FIG. 7 is a diagram of areas used in the sensor in two modes.
Figure 7:
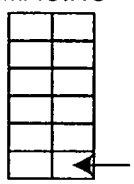
Figure 7:
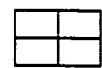

Data acquisition with the digital X-ray sensor 14 is explained below. Among the imaging elements in the two-dimensional detection plane of the digital X-ray sensor 14 (refer to FIG. 8), the CPU 19 selects, according to the imaging mode, imaging elements which detect signals as an object of image reconstruction and acquires signals only from the selected imaging elements. Because the image data are not read out from unnecessary imaging elements which depend on the imaging mode, the digital X-ray imaging sensor can be used efficiently depending on imaging mode, and image data of an optimum data capacity can be acquired for each imaging mode. For example, as shown schematically in FIG. 7, the sensor area necessary for panoramic imaging is long in vertical direction and is narrow relative to that necessary for CT imaging. Therefore, the necessary sensor area depends on the imaging mode. Then, according to the imaging mode, the irradiation field is changed with the primary and secondary slit mechanisms 12, 16, and imaging elements for detecting signals necessary for image reconstruction are selected among the imaging elements in the two-dimensional detection plane 13e of the digital X-ray sensor 14. Thus, without changing the digital X-ray sensor 14, the imaging area and the imaging elements to be read out can be changed according to the imaging mode. (In the schematic example shown in FIG. 8, wherein in the imaging with a narrow slot irradiation field shown at the right side, data are not read out from the imaging elements displayed with hatching, in contrast to the imaging in a wide irradiation field at the left side, so that a ratio of the number of imaging elements use is a third.) In order to narrow the imaging area, a dose of radiation to the object can be suppressed. In the case of the imaging in a wide irradiation field at the left side, the area R3 or the entire area of the two-dimensional detection plane 13e is used, while the area R1 or a central area of a third of the entire area in the two-dimensional detection plane 13e is used.

Further, because data are not read out from unnecessary imaging elements, data read-out time (data acquisition time) can be shortened (in the schematic example shown in FIG. 8, the ratio of read-out time becomes 1/3 similarly to that of pixels), and a time for reconstructing an image is also shortened. As a result, a reconstruction image can be obtained and displayed in a shorter time. For example, it is assumed that the X-ray imaging apparatus "M" rotates the rotary arm (supporter) 4 in a circle around an object in eighteen seconds and acquires image data of 512 sections. Then, if panoramic imaging is performed with the same apparatus, because the area in the digital X-ray sensor 14 is decreased to a third of the entire area, 512 images can be acquired in six seconds which is a third of the time in CT imaging. Thus, by changing an area for the image read-out in the digital X-ray sensor according to imaging mode, image data of an appropriate amount can be acquired in a suitable time for each imaging mode. Then, the imaging efficiency becomes good. In an imaging mode using a small region of interest to be imaged, a time for acquiring image data can be shortened on an imaging region in an object.

Figure 8:
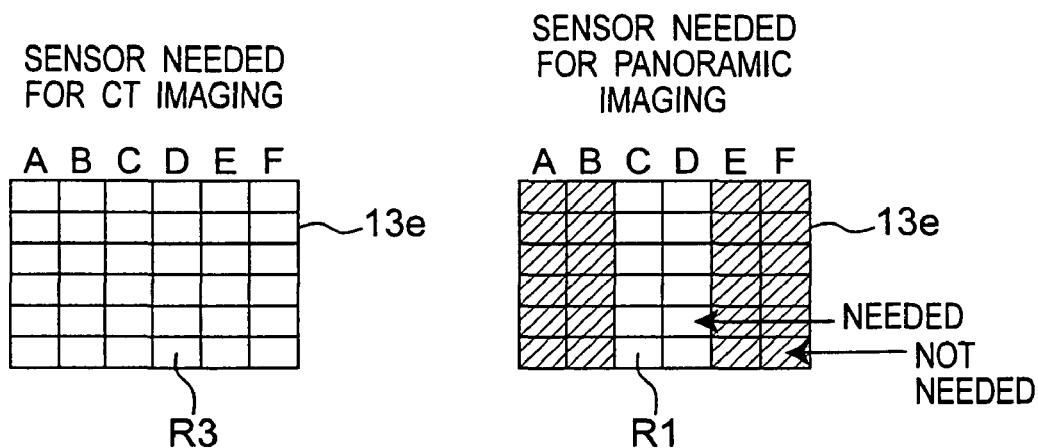
FIG. 8 is a diagram for reading data in the two imaging modes.
Figure 9:
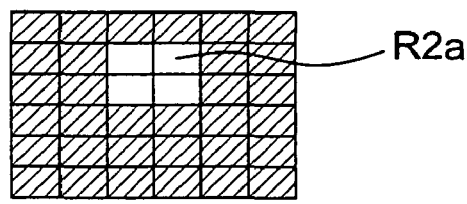
FIG. 9 is a diagram on imaging in a limited irradiation field in the two-dimensional detection plane in the digital X-ray sensor.
Figure 9:
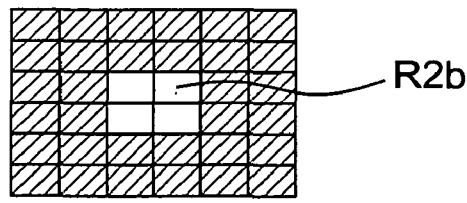
Figure 9:
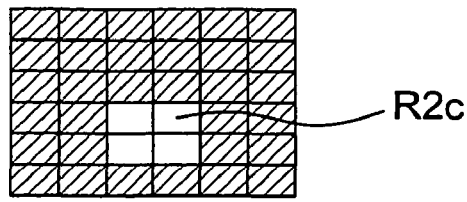

In CT imaging, an entire area of the two-dimensional detection plane 13e such as area R3 shown in FIG. 8 can be used. However, as shown in FIG. 9, the scanning can be performed with a limited irradiation field. In an example shown in FIG. 9, areas R2a to R2c having a third of the entire area R1 shown in FIG. 8 can be set. The areas R2a to R2c have the width equal to that of the area R1, but have the height of a third of the area R1. The area R2b is located at the center of the two-dimensional detection plane 13e, the area R2a is positioned above the area R2b, and the area R2c is positioned below the area R2b. Thus, by using a part of the sensor, CT imaging can be performed with a smaller irradiation field.

It is to be noted that FIGS. 8 and 9 are schematic drawings used to explain that a plurality of read-out areas can be set in the two-dimensional detection plane 13e. Therefore, they do not reflect the number of imaging elements or image read-out areas used actually for the two-dimensional detection plane 13e. For example, in FIGS. 8 and 9, the imaging elements are arranged in nine elements in a row and in nine ones in a column. However, the density of imaging elements in an actual two-dimensional detection plane 13e is much higher, and it forms a two-dimensional array of a much larger number in vertical and horizontal directions. The width of area R1 in FIG. 8 and those of R2a to R2c in FIG. 9 are displayed to be the same each other, but the width of an actual area in CT imaging with a smaller irradiation field is much wider than that of an area for panoramic imaging. As will be explained later, the actual read-out range is for example 10 mm times 150 mm in panoramic imaging, while 60 mm times 60 mm in CT imaging with the smaller irradiation field.

When one of the structures shown in FIGS. 14, 15, 18A and 18B to be explained later is used to limit the irradiation field to a part of the two-dimensional detection plane 13e and to shift it in the two-dimensional detection plane 13e, data can be read out from the limited range R2a to R2c, as explained above. Then, CT imaging can be performed in a time of a third of the time needed for read-out from area R1. Though the areas R2a to R2c are defined to have three levels of height, only two steps of R2a and R2c may be set, or more height levels may be set.

Next, data processing in various imaging modes is explained in detail. In an imaging such as CT imaging which uses a wide sensor, image data are read from all the imaging elements (for example, 150 mm times 150 mm) to reconstruct an image. In the CT imaging, the rotary arm (supporter) 4 is rotated by driving a rotary device 7 according to the motor drive signal during the imaging, so that the X-ray source 9 and the digital X-ray sensor 14 are rotated or moved around an object. The X-ray source 9 generates an X-ray cone beam, and the X-rays transmitting the object are detected with the digital X-ray sensor 4 having the two-dimensional detection plane 13e. The image reconstructor 23 reconstructs an image based on the acquired X-ray image data. In cephalometric imaging, a head of an object is fixed to keep the position relationship between the X-ray source and the object in a constant condition. A cassette of the digital X-ray sensor 14 is set at a position for cephalometric imaging (not shown). Then, X-rays are detected in the entire two-dimensional detection plane 13e of the digital X-ray sensor 14. As will be explained later, the imaging is repeated by shifting the cassette in the horizontal direction. Then, the image reconstructor 23 creates an X-ray image in a wide area based on the image data acquired with all the imaging elements in the digital X-ray sensor 14.

For cephalometric imaging, the two-dimensional detection plane 13e of the digital X-ray sensor 14 may be set to have an area of an appropriate size. Examples are shown in FIG. 10 (a) to (c).

Figure 10:
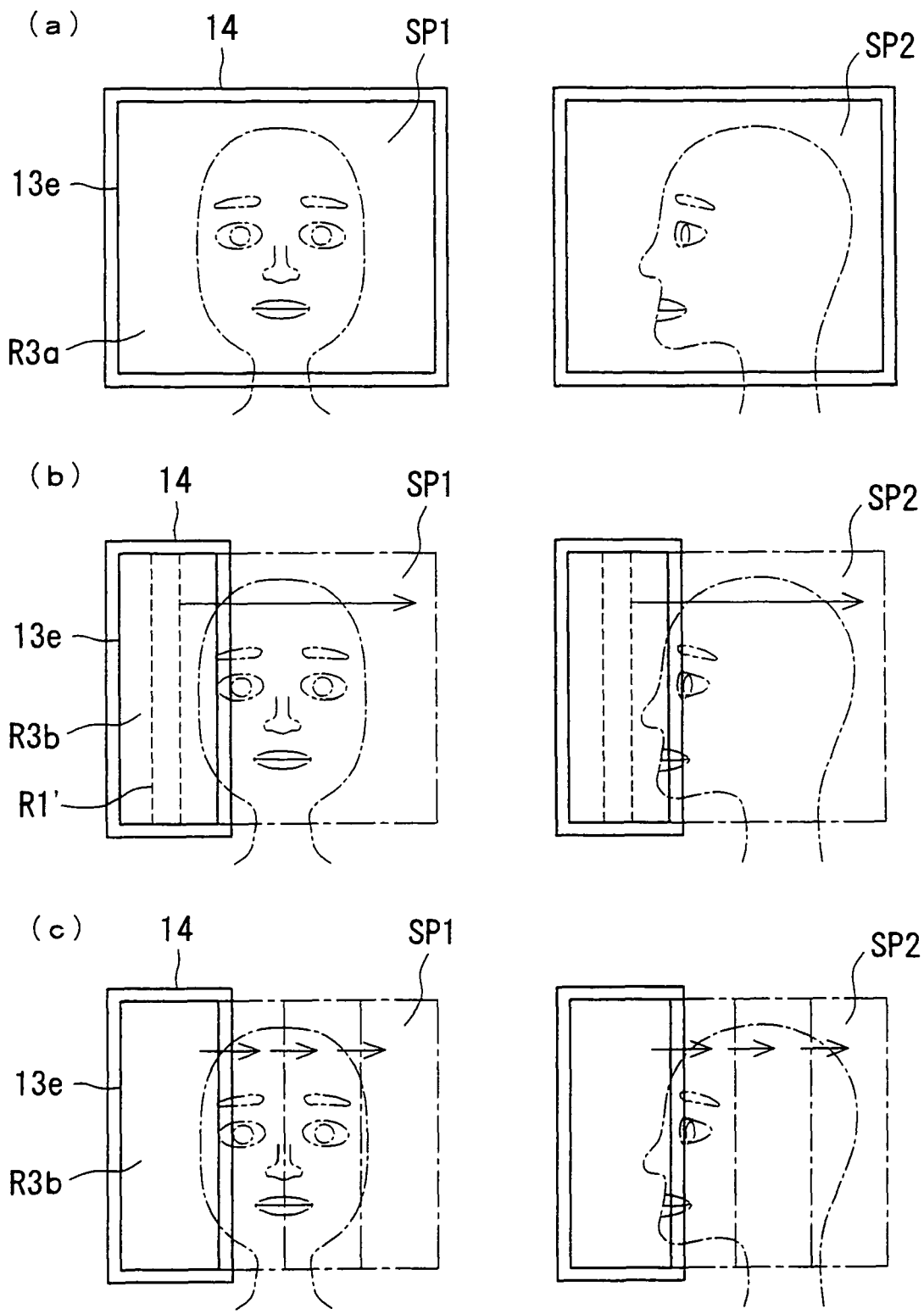
FIG. 10 is a diagram on cephalometric imaging in a limited irradiation field in the two-dimensional detection plane in the digital X-ray sensor.

In the digital X-ray sensor 14 shown in FIG. 10 (a), the two-dimensional detection area 13e has an area, sufficiently wide to image the entire head of a person as an object at a time, for example, an area of 200 mm vertically and 260 mm horizontally. In concrete, the front of a head can be contained in a detection plane having an area of 221 mm in vertical direction and 202 mm in horizontal direction, and the side of the head can be contained in a detection plane having a range of 221 mm in vertical direction and 252 mm in horizontal direction. If such a detection plane is available, the imaging can be performed in an area SP1 containing the front of the entire head and in another area SP2 containing the side of the entire head. Therefore, if the digital X-ray sensor 14 has the two-dimensional detection plane 13e having a size of 221 mm in the vertical direction and 252 mm in the horizontal direction, all of the above-mentioned imaging modes, including the above-mentioned CT imaging, CT imaging with a limited irradiation field, panoramic imaging, cephalometric imaging and transmission imaging in a wide range, is possible by using the entire area or partial areas.

The two-dimensional detection plane 13e of the digital X-ray sensor 14 shown in FIG. 10(b) has a height sufficient to include a person's head, but has a width narrower than that of the two-dimensional detection plane 13e shown in FIG. 10(a). The entire area of the detection plane 13e is denoted as area R3b. By using an area R1∝ longer in the vertical direction as an area for reading the data, X-ray imaging is continued while moving the area R1' in the horizontal direction without stopping. By moving the area R1', an X-ray image of the entire area SP1, SP2 can be obtained. A panoramic image may be taken by using a part of the area R1' as an area for reading the data.

The digital X-ray sensor 14 shown in FIG. 10(b) has the same two-dimensional detection plane 13e as that shown in FIG. 10(b). In this example, the area R3b is moved successively from left to right in the drawing several times. X-rays are irradiated for each movement to construct an entire X-ray image in the entire area SP1, SP2. Alternatively, the area may be moved continuously, similarly to FIG. 10(b), without intermittent movement. Further, a panoramic image may be taken by using a part of the area R3b similarly to FIG. 10(b).

In the digital X-ray sensors 14 shown in FIGS. 10(b) and (c), the height is larger than the width, and the sensor is moved laterally. Alternatively, the width is larger than the height, and the sensor is moved vertically.

In the orthographic projection panoramic imaging the XY table 8 moves the rotary shaft 4a of the rotary arm (supporter) during the imaging so that a narrow beam is projected from the X-ray source 9 in a direction generally perpendicular to the dental arch. The CPU 19 controls the motor drive signal 20 to rotate the rotary arm 4 and controls the XY table 8 to move the X-ray source 9 and the digital X-ray sensor 14 along the locus of the panorama imaging. As the rotary shaft 4a is moved, its center is shifted continuously along the locus of the panoramic imaging. In a narrow range imaging such as panoramic imaging, the irradiation field of X-rays is limited, and the area (read-out area) from which image data are read is limited as shown in FIG. 8. The image reconstructor 23 reconstructs a panoramic image by superposing the image data read by a portion at a time while shifting the position thereof. Thus, only a partial area in the digital X-ray sensor 14 is used, and unnecessary read out from the storage device can be omitted. Therefore, the capacity of image data to be read does not needed excessively large, and a time for reading an image can be shortened, so that the times necessary for the acquisition and for the display of a reconstruction image can be shortened. In the above-mentioned explanation and in FIG. 8, a ratio of the area from which image data are read out, as an example for explanation, for CT imaging and panoramic imaging is set to CT imaging:panoramic imaging=1:3. In a panoramic imaging, for example, a narrow sensor area as wide as, for example, 10 mm times 150 mm is used for reading image data. In this case, the image read-out time for each image is shortened by a ratio of 1/15 relative to the CT imaging using an area of 150 mm times 150 mm if the number of images to be acquired is the same. Therefore, if the frame rate in panoramic imaging is increased by a ratio in a range from 1 to 15, the image read-out time can be increased to obtain a sharper image in a degree that the time necessary for acquiring and reconstructing an image and the capacity of image data do not become excessively longer and larger.

Further, in a cross tomography imaging as an example of imaging using a wide area sensor, the X-ray sensor 9 and the digital X-ray sensor 14 are moved at a constant speed while keeping them to oppose to each other while interposing a region of interest as an object. The XY table 8 positions the rotary arm (supporter) 4 to interpose the region of interest (a section) and rotates the rotary arm 4 to move the X-ray sensor 9 and the digital X-ray sensor 14 relative to an object in a dental arch. An X-ray image is taken for each of a predetermined amount of movement to acquire image data or frame images each having an imaging angle relative to the section shifted little by little, and it is stored in a storage device. Then, the image reconstructor 23 operates the image data to reconstruct an image of the section. In the cross tomography imaging, a wider area in the digital X-ray sensor 14 than the area in panoramic imaging is used. Therefore, in an X-ray imaging apparatus wherein one of cross tomography imaging and panoramic imaging can be selected by changing the area used in the sensor, the capacity of image data can be made optimum and the time needed to reconstruct an image can be shortened.

In cephalometric imaging, two modes, that is, a mode using a wide area sensor and another mode using a narrow area sensor are available. During cephalometric imaging, the X-ray source 9 and the digital X-ray sensor 14 are positioned to keep a prescribed distance while interposing an object between them, and the digital X-ray sensor 9 irradiates the object. In the mode using a wide area sensor, the digital X-ray sensor 14 is fixed, and transmitted X-rays are detected in the entire area in the sensor 14. Then, the X-ray transmission data are read from the digital X-ray sensor 14 at a time and reconstructs and displays an image. On the other hand, in the mode using a wide area sensor, a part (for example, 10 mm times 150 mm) of the detection plane in the digital X-ray sensor 14 is used. Therefore, by driving the digital X-ray sensor 14 mechanically, the transmission X-rays are detected in the part and sends the data to the video memory at necessary times. The dose to the object can be suppressed by irradiating the object with a long and narrow beam having an area as minimum as necessary controlled by the slit controller 12a when the direction or the position of the X-ray source 9 is driven by the X-ray source driver (not shown) according to the mechanical drive of the digital X-ray sensor 14 in up and down directions and in right and left directions.

As explained above, in the cephalometric imaging using a wide area sensor, because the entire area in the digital X-ray sensor 14 is used, the read out time of image data is long, but the irradiation time itself can be shortened with an irradiation beam of wide area. Further, it is not needed to provide a driver for driving the sensor 14 mechanically. Thus, the cost and the weight are saved.

Further, in dental imaging, the X-ray source 9 and the digital X-ray sensor 14 are opposed to each other, while interposing teeth between them, and the XY table 8 moves the rotary shaft (supporter) 4 so as to take an image including one to three teeth as an object, and the rotary arm 4 is rotated. Then, the X-ray source 9 irradiates the object with X-rays, and the digital X-ray sensor 14 detects the X-rays transmitting the object. The irradiation field of X-rays is set by the primary slit mechanism 12 only to an area (for example, 20 mm times 30 mm) necessary for digital imaging. The area used in the digital X-ray sensor 14 is also limited to an area necessary for dental imaging. The CPU 19 reads only the mage data detected by the imaging elements used for dental imaging, and the image reconstructor 23 reconstructs an X-ray image based on the image data. Thus, in the dental imaging, too, the dose can be suppressed to a level as low as necessary, and the time for acquiring, reconstructing and displaying an image can be shortened.

The above-mentioned various imaging modes are compared below. In CT imaging, image data are read from the entire area in the two-dimensional detection area in the digital X-ray sensor 14. In an example shown schematically in FIG. 8, numerical signs "A" to "F" denote a column of imaging elements, and all the columns are read. Therefore, data is read on the entire columns repeatedly in an order such as ABCDEFABCDEF. On the other hand, in panoramic imaging, only a part (in FIG. 8, columns C and D without hatching) is used for reading image data. Thus, data are read only on the two columns in an order of CDCDCDCDCDCD. That is, in panoramic imaging, the columns A, B, E and F in FIG. 8 are not used for reading image data, and only necessary columns (columns C and D without hatching) are used for reading image data. Thus, the frame rate (a number of images to be read per unit time) can be increased by using a part of the imaging elements. When the same clock signal generator 28 is used, columns C and D can be read three times in panoramic imaging while columns A to F are read once in CT imaging. Thus, the image data can be superposed, and the image quality can be increased.

Figure 11:
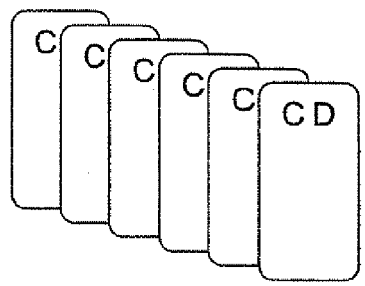
FIG. 11 is a diagram of superposition of data.

In a schematic example shown in FIG. 11, the columns are read on panoramic imaging in an order of CDCDCDCDCD-CDCD. When the image data (frame data) on the columns C and D are obtained, the imaging position of the object is shifted as time passes. Then, by synchronizing the moving speed of the digital X-ray sensor with the read-out speed thereof in the unit of imaging element, image data on the same object position can be acquired a plurality of times. For example, if the data on column D in the first time is acquired on the same object position as the data on column C in the second time, they are accumulated so that image data can be acquired. By accumulating the acquired data on the same object position, a smooth panoramic image can be obtained (refer to JP-B H02-029329).

Figure 12A:
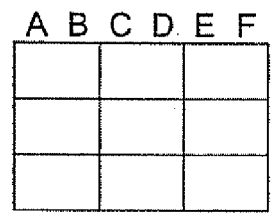
FIG. 12A is a diagram of an example of binning.
Figure 12A:
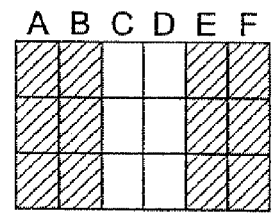

If necessary, as shown in FIG. 12A, a device for combining imaging elements or a binning processor is provided for combining X-ray image data on a plurality of adjacent imaging elements in the digital X-ray sensor 14 to be dealt as a pixel. In an example shown in FIG. 12, 1*2 imaging elements are combined in panoramic imaging, while 2*2 imaging elements are combined in CT imaging. Therefore, image data can be acquired with a number of pixels in a range (6 in FIG. 12) finer than the counterpart in CT imaging (9 in FIG. 12). Thus, in CT imaging the time for reading image data and the time for reconstructing an image can be shortened relative to the normal process on pixels without the binning, while in panoramic imaging, the time for reading image data and the time for reconstructing an image can be kept shorter than the counterparts in CT imaging.

Figure 12B:
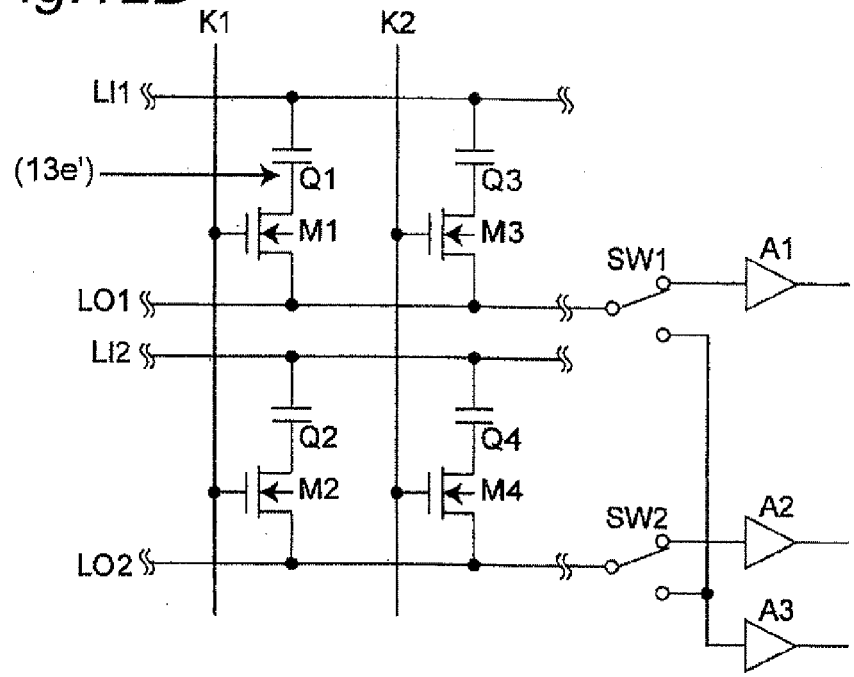
FIG. 12B is a reduced circuit diagram for four pixels in a MOS sensor.

FIG. 12B shows a simplified circuit only on four pixels in a MOS sensor. The partial circuit has four imaging elements 13e' adjacent to each other like a lattice between lines LI1 and LO1 and between lines LI2 and LO2. The four imaging elements has capacitors Q1 to Q4, MOS transistors M1 to M4 for reading charges stored in the capacitors Q1 to Q4, sense amplifiers A1 to A3, and switches SW1 and SW2 for connecting the sense amplifiers A1 to A3 to lines LO1 and LO2. The transistors M1 to M4 and the switches SW1 and SW2 are components of a device for combining signals of a plurality of adjacent imaging elements 13e' to be dealt as a pixel.

When a normal imaging is performed with this circuit, the switches SW1 and SW2 are controlled first to connect the lines LO1 and LO2 to the sense amplifiers A1 and A2. After an image is taken, the line K1 is activated to read the charges in the capacitors Q1 and Q2 to the lines LO1 and LO2. Voltage signals of the sense amplifiers A1 and A2 are converted to digital signals by sampling them with analog-to-digital converters not shown. After the lines LO1 and LO2 are discharged once, the line K2 is activated. Then, voltage signals in correspondence to the charges in the capacitors Q3 and Q4 are generated by the sense amplifiers A1 and A2, and they are sampled and converted to digital signals. Thus, the charges in the capacitors Q1 to Q4 in the imaging elements in the MOS sensor are converted to digital signals.

In the case of 2*1 binning, the switches SW1 and SW2 are controlled to connect the lines LO1 and LO2 to the sense amplifiers A1 and A2. After an image is taken, the two lines K1 and K2 are activated simultaneously to read the charges in the capacitors Q1 and Q3 to the line LO1 to be superposed or combined as one pixel, and to read the charges in the capacitors Q2 and Q4 to the line LO2 for superposition or combination as one pixel. Then, the sense amplifier A1 generates a voltage signal of a pixel based on a sum of the charges Q1 and Q3 after the superposition, while the sense amplifier A2 generates a voltage signal of a pixel based on a sum of the charges Q2 and Q4 after the superposition or combination. Then, the voltage signals are sampled and converted to digital signals.

In the case of 1*2 binning, the switches SW1 and SW2 are controlled to connect the lines LO1 and LO2 to the sense amplifier A3. After an image is taken, the line K1 is activated to read the charges in the capacitors Q1 and Q2 to the lines LO1 and LO2 short-circuited to each other for superposition or combination. Then, the sense amplifier A3 generates a voltage signal of a pixel based on a sum of the charges Q1 and Q2 after the superposition or combination. Then, the voltage signal is sampled and converted to a digital signal. Then, after the lines LO1 and LO2 are discharged once, the line K2 is activated to read the charges in the capacitors Q3 and Q4 to the lines LO1 and LO2 for superposition or combination as one pixel. Then, the sense amplifier A3 generates a voltage signal of a pixel based on a sum of the charges Q3 and Q4 after the superposition or combination. Then, the voltage signal is sampled and converted to a digital signal.

In the case of 2*2 binning, the switches SW1 and SW2 are controlled to connect the lines LO1 and LO2 to the sense amplifier A3. After an image is taken, the lines K1 and K2 are activated simultaneously to read the charges in the capacitors Q1, Q2, Q3 and Q4 to the lines LO1 and LO2 short-circuited to each other for superposition or combination as one pixel. Then, the sense amplifier A3 generates a voltage signal of a pixel based on a sum of the charges Q1, Q2, Q3 and Q4 after the superposition or combination. Then, the voltage signals are sampled and converted to digital signals.

Figure 13:
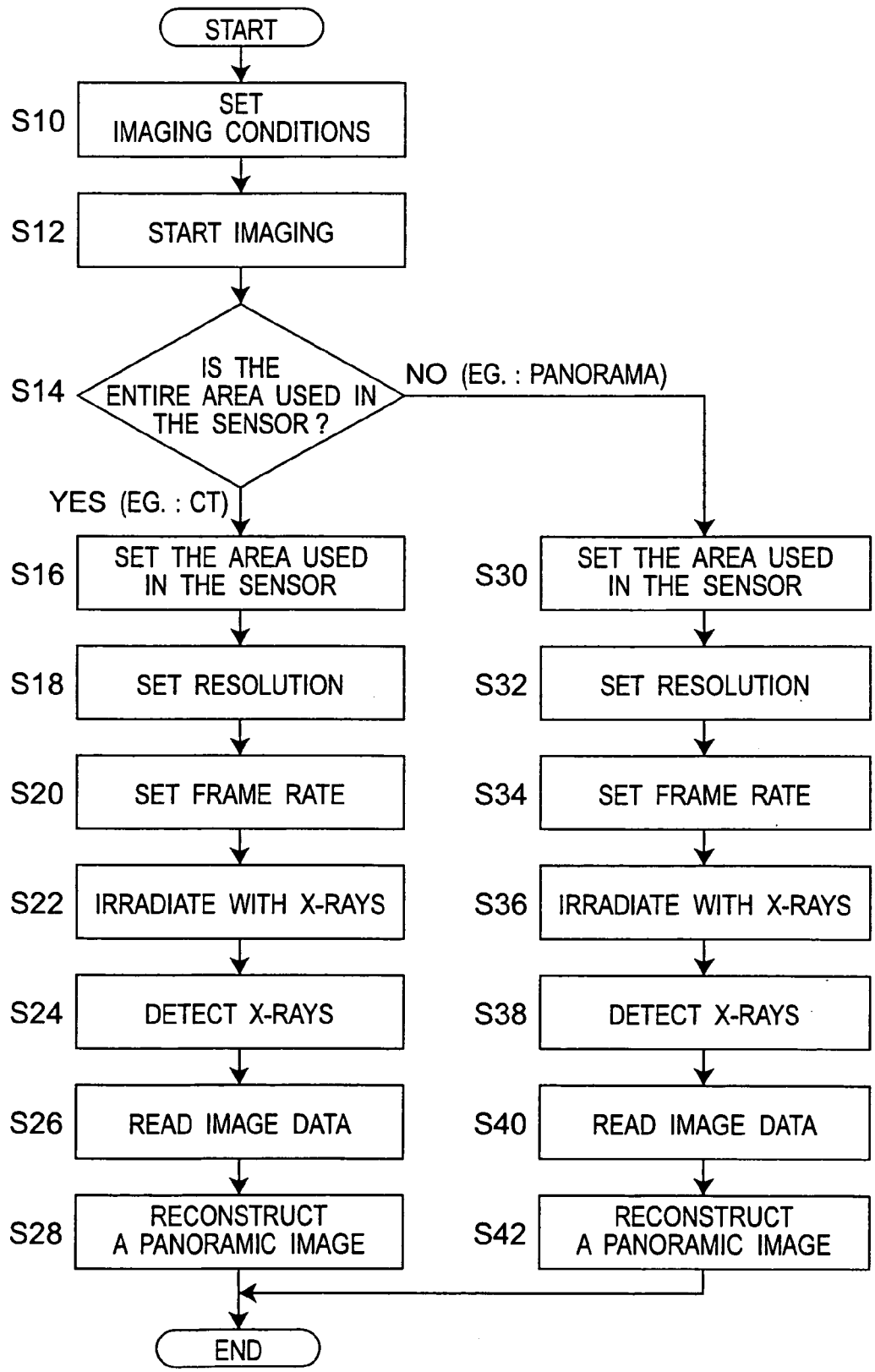
FIG. 13 is a flowchart for selecting an imaging mode and for reconstructing an image.

FIG. 13 shows an example of a flowchart for selecting an imaging mode and for reconstructing an image. Wide range imaging such as CT imaging and narrow range imaging such as panoramic imaging can be selected with the operation unit 17A. After various imaging conditions are set with the operation panel 17 by an operator (step S10), a start instruction for imaging is received (S12). Then, it is decided whether an area used in the sensor is entire or not (S14).

If the entire area is decided to be used (in this example, CT imaging), the area used in the sensor is set (S16), the resolution of the image is set (S18), and the frame rate of image data is set (S20). The area used for reading image data in narrow region imaging is, for example, area R1 shown in FIG. 8, and it is narrower than an area used for wide region imaging, for example, area R3 shown in FIG. 8. In step S10, a mode is also selected among a first imaging mode or narrow region imaging and a second imaging mode or wide region imaging having different irradiation fields for X-rays. The operation unit 17 is used as an image mode selector.

Examples of the first and second imaging modes are as follows.

(1) The first imaging mode is CT imaging which uses the entire area in the two-dimensional detection plane 13e, and the second imaging mode is one of panoramic imaging imaging, cephalometric imaging (the case shown in FIG. 10(b)) and dental imaging.

(2) The first imaging mode is CT imaging which uses the entire area in the two-dimensional detection plane 13e, and the second imaging mode is CT imaging which uses a part of the area in the two-dimensional detection plane 13e (3) The first imaging mode is CT imaging which uses a part of the area in the two-dimensional detection plane 13e, and the second imaging mode is one of panoramic imaging imaging, cephalometric imaging (the case shown in FIG. 10(b)) and dental imaging.

(4) The first imaging mode is cephalometric imaging, and the second imaging mode is panoramic imaging. However, the combination of the two imaging modes is not limited as far as the irradiation field of X-rays in the second imaging mode and the area for reading image data in the digital X-ray sensor 14 are narrower than the counterparts in the first imaging mode.

Next, an image is taken. The X-ray source 9 generates an X-ray cone beam (S22), and the X-rays are detected with the digital X-ray sensor 14 (24). This is continued, for example, while the X-ray source 9 and the digital X-ray sensor 14 are rotated around the object by one turn. Then, the acquired image data (X-ray projection data) is read from the imaging elements in the digital X-ray sensor 14 (S26), and the image reconstructor 23 reconstructs a CT image (S28).

Further, if the area used in the sensor is not the entire area (in this example, panoramic imaging) (NO at S14), the area used in the sensor is set (S30), and the resolution is set (S32), and the frame rate is set (S34). Next, an image is taken. The X-ray source 9 generates an X-ray cone beam (S36), and the X-rays are detected with the digital X-ray sensor 14 (38). This is continued, for example, while the X-ray source 9 and the digital X-ray sensor 14 are moved along the locus for panoramic imaging. Then, the acquired image data (X-ray projection data) is read from the imaging elements in the digital X-ray sensor 14 (S40), and the image reconstructor 23 reconstructs a CT image (S42).

In the X-ray imaging apparatus explained above, the rotary arm (supporter) 4 normal to the rotary shaft is used. However, instead of the rotary shaft (supporter), a C-arm may be used having a horizontal rotary shaft for rotating the X-ray source and the digital X-ray sensor while a patient lies on a bed. Needless to say, besides the above-mentioned rotary arm and the C-arm, a device for supporting and rotating the X-ray source and the digital X-ray sensor may have various modifications, such as a combination of a round base and a pair of supporting columns extending upward from the periphery of the base.

Figure 14:
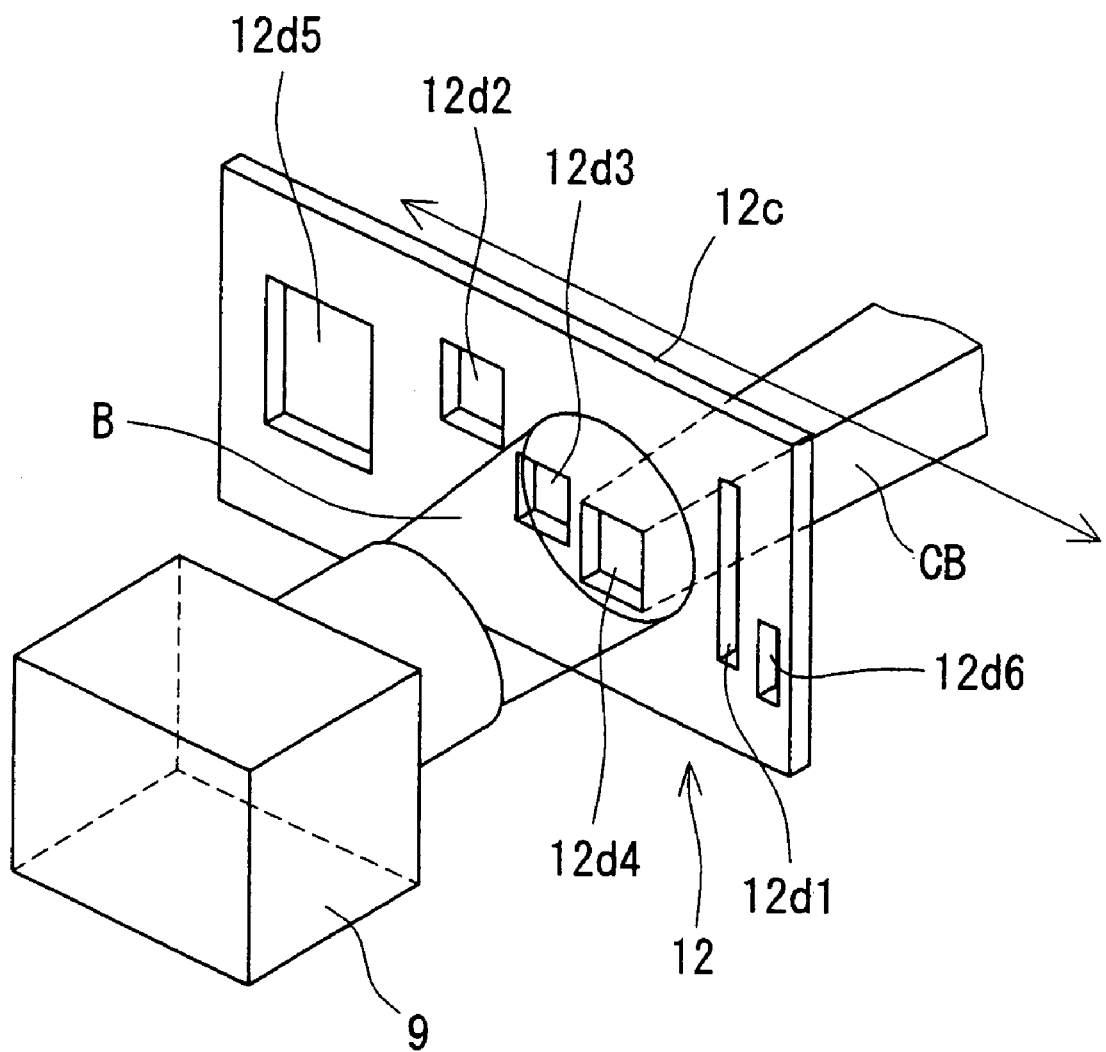
FIG. 14 is a diagram for changing a position of an irradiation field.
Figure 15:
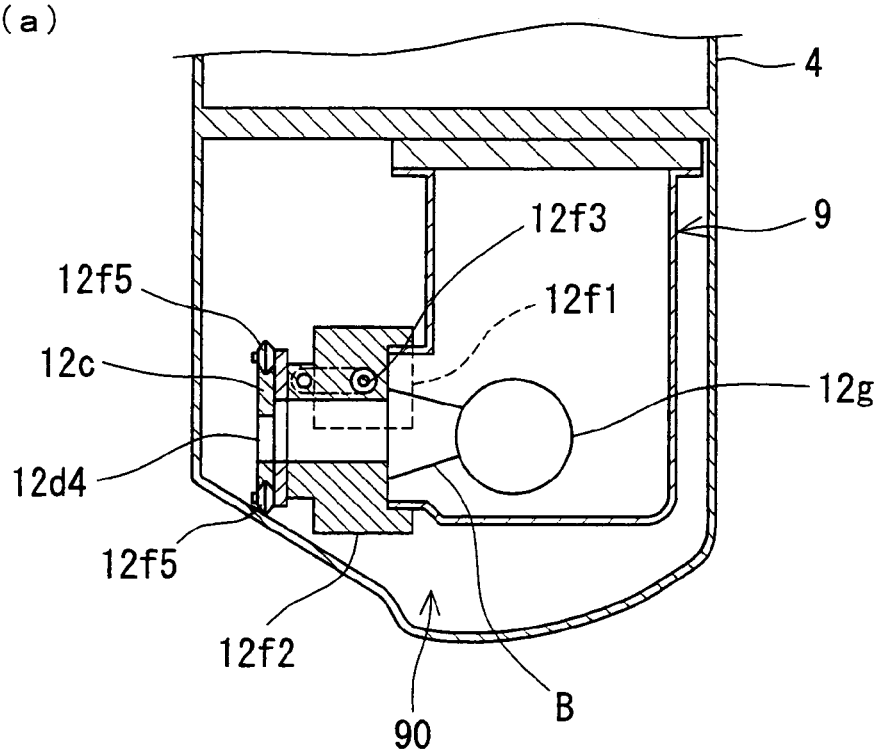
FIG. 15 is another diagram for changing a position of an irradiation field.
Figure 15:
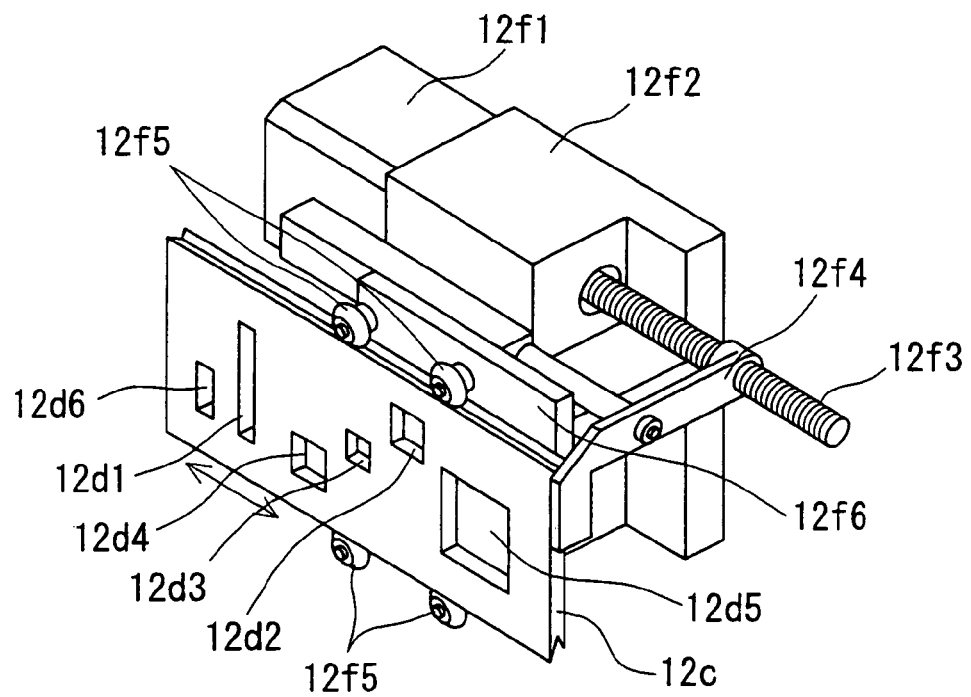

Next, an X-ray imaging apparatus which uses the above-mentioned basic structure is explained. FIGS. 14 and 15 shows a basic structure of an X-ray generator unit 90 having the X-ray source 9 and the primary slit mechanism 12 in a first attachment 30 in the rotary arm (supporter) 4. FIG. 15(a) shows a section in the X-ray generator unit 90 in the X-ray source 9, and FIG. 15(b) shows the primary slit mechanism 12 in a perspective.

As shown in FIG. 14, a slit plate 12c as a component of the primary slit mechanism 12 is provided in the irradiation direction of the X-ray source 9. As shown in FIG. 15(a), the X-ray source 9 generates an X-ray cone beam B with an air-cooled X-ray tube (for example, tube voltage 90 kV and tube current 10 mA). The primary slit mechanism 12 is used as a device for changing the irradiation field. The slit plate 12c in the primary slit mechanism 12 is slid in right-and-left direction by a motor 12f1, as shown in FIG. 15(b). The slit plate 12c has five slits 12d1 to 12d5. The slit 12d1 has a shape longitudinal in parallel to the axial direction of the rotary shaft 4a, in correspondence to the area R1 in the two-directional plane of the digital X-ray sensor 14. The slits 12d2, 12d3 and 12d4 correspond to areas R2a, R2b and R2c in the two-dimensional plane in the digital X-ray sensor 14, respectively, and they have different heights of irradiation field in parallel to the axial direction of the rotary shaft. The slit 12d5 corresponds to area R3 in the two-dimensional detection plane of the digital X-ray sensor and has a larger area than any of the slits 12d2 to 12d4. Because the slits 12d1 to 12d5 are arranged in the lateral direction in the slit plate 12c, the irradiation field of X-ray beam B is changed as the slit plate 12c is moved laterally to the optical axis of the X-ray beam, by regulating the range of the X-rays with the slit. The shape of the slit plate 12c is not limited.

As mentioned above, the width of area R1 in FIG. 8 is the same as those of R2a to R2c in FIG. 9, for the convenience of the drawings. However, the width of an actual area in CT imaging with a smaller irradiation field is much wider than that of an area for panoramic imaging. The actual read-out area R1 is for example 10 mm times 150 mm in panoramic imaging, while the actual read-out areas R2a to R2c for CT imaging with a smaller irradiation field are for example 60 mm times 60 mm.

In the situation shown in FIG. 14, the X-ray beam B is regulated with the slit 12d4, and an X-ray beam in correspondence to area R2c is irradiated from the X-ray source 9 forward and somewhat downward. The slit 12d2 is used to regulate the X-ray beam in correspondence to area R2a, similarly to the slit 12d4, but it is provided at a higher position than the slit 12d4. It is used to generate an X-ray cone beam CB forward and somewhat upward. The slit 12d3 is used to regulate the X-ray beam in correspondence to area R2b, similarly to the slits 12d4 and 12d2, but it is provided at an intermediate position between the slits 12d4 and 12d2. It is used to generate an X-ray cone beam CB forward and straight. By selecting one of the slits 12d2 to 12d4, the primary slit mechanism 12 changes the position of irradiation field of X-ray beam B in a direction parallel to the axial direction of the rotary shaft.

Instead of the areas R2a to R2c defined at three levels of height, only two steps of R2a and R2c may be provided, or more levels may be provided. Further, the number of slits provided in the slit plate 12c may be adapted according to the number of the areas, and it is not limited to a particular number.

Further, the slit plate 12c may have a slit 12d6 for a cephalometric imaging. Further, as mentioned above, the vertical size of the digital X-ray sensor 14 may be sufficiently large to be used for panoramic imaging and for cephalometric imaging. In this case, the area R1 is used for a cephalometric imaging, while a part of the area R1 is used for panoramic imaging. The slit 12d6 has a shape longitudinal in the direction in parallel to the axial direction of the rotary shaft 4a, in correspondence to the area R1. The X-ray beam B passing the slit 12d1, 12d6 becomes a long and narrow X-ray beam, and the X-ray beam B passing one of the slits 12d2 to 12d5 becomes an X-ray cone beam CB.

FIG. 15(a) shows a structure of the first attachment 30 in detail. Inside the first attachment 30, the X-ray source 9 is fixed to the rotary arm (supporter) 4. The X-ray beam B is radiated from the air-cooled X-ray tube 12g inside the X-ray source 9, and it is regulated by one of the slits 12d1 to 12d6 in the slit plate 12c provided before the X-ray source 9 and is radiated forward.

Next, the primary slit mechanism 12 is explained. A block 12f2 fixed to the X-ray source 9 has a throughhole through which the X-ray beam is allowed to pass. A motor 12f1 is fixed to the block 12f2. A drive shaft 12f3 is a screwed shaft driven and rotated by the motor 12f1. A member 12f4 to be driven is displaced relative to the fixed block 12f2 with the drive shaft 12f3 in a direction crossing the X-ray beam B. A plate 12f6 for mounting rollers 12c is fixed before the solid block at a position not preventing the passage of the X-ray beam B from the X-ray source 9. The slit plate 12c is guided by four rollers 12f5 arranged on the plate 12f6, and it is fixed to the member 12f4 so as to be displaced with the member 12f4 in the direction crossing the X-ray beam B. A part of the member 12f4 is screwed, and it is engaged with a drive shaft 12f3. By driving the member 12f4 by the drive shaft 12f3, the member 12f4 is displaced in the axial direction of the drive shaft 12f3, and the slit plate 12c is displaced in the axial direction of the drive shaft 12f3. By displacing the slit plate 12c, one of the six slits 12d1 to 12d6 can be selected.

The irradiation field of the X-ray beam B corresponds to one of the slits 12d1 to 12d6 selected with the primary slit mechanism 12. Especially, when one of the slits 12d2 to 12d4 is selected, the irradiation field is regulated to have the same size, and the X-ray cone beam regulated to have the same size of irradiation field is shifted on the digital X-ray sensor 14 in a direction in parallel to the axial direction of the rotary shaft 4a.

Figure 16:
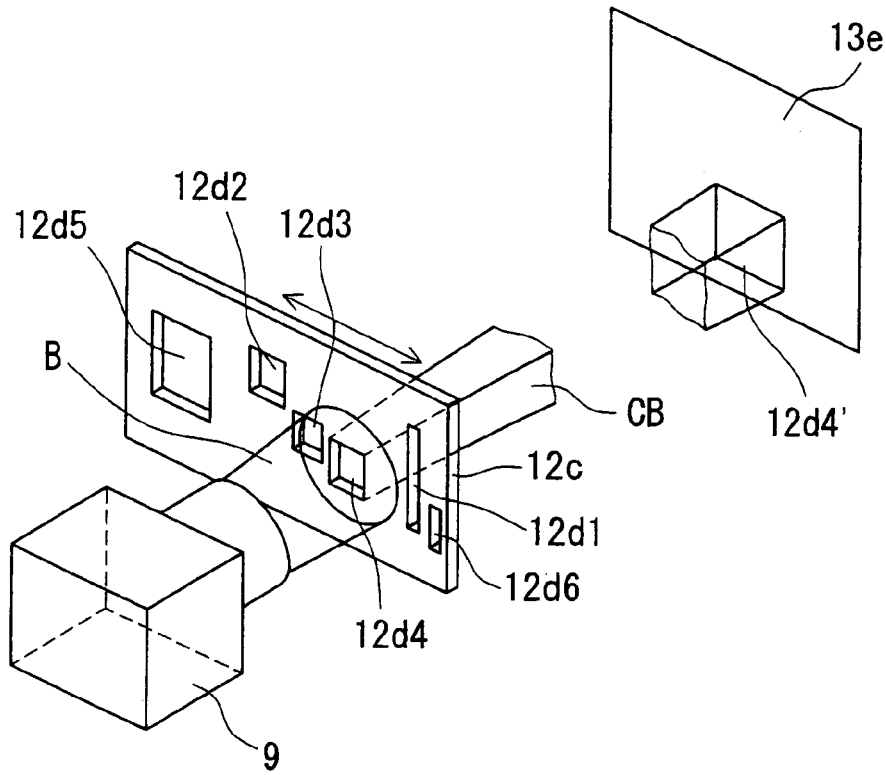
FIG. 16 is a still another diagram for changing a position of an irradiation field.
Figure 16:
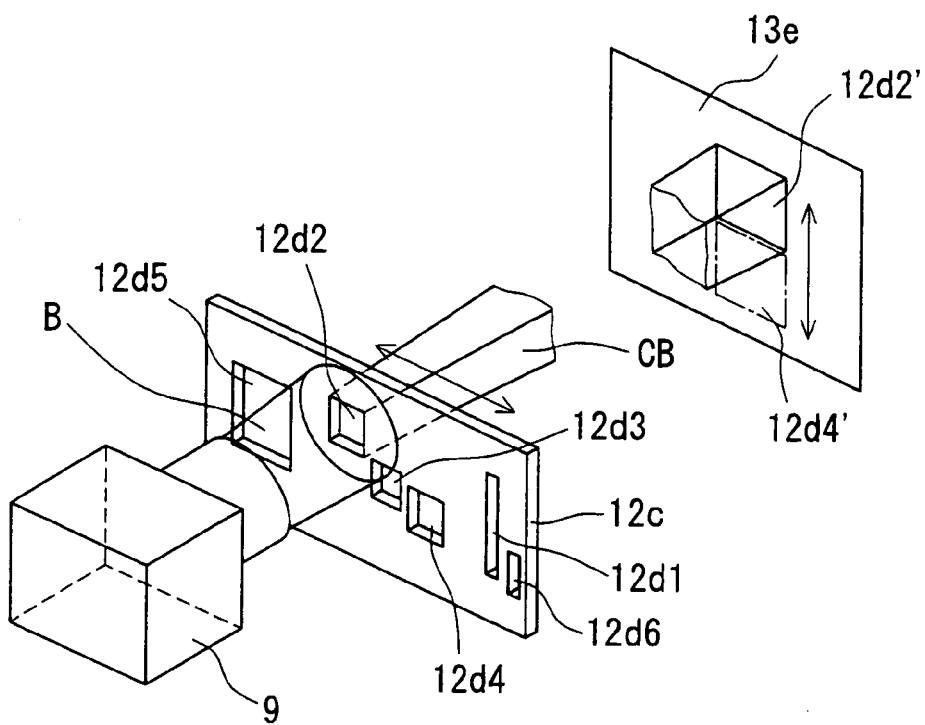

FIG. 16 shows situations where the direction of X-ray cone beam CB is shifted with the slit plate 12c of the primary slit mechanism 12 shown in FIG. 15 in a direction in parallel to the rotary shaft 4a. In FIG. 16(a), the X-ray cone beam B passing through the slit 12d4 becomes an X-ray cone beam CB, and it is irradiated in an irradiation field 12d4' at the center and somewhat low in the two-dimensional detection plane 13e. In FIG. 16(b), the X-ray cone beam B passing through the slit 12d2 becomes an X-ray cone beam CB, and it is irradiated in an irradiation field 12d2' at the center and somewhat high in the two-dimensional detection plane 13e. The irradiation field 12d2' may be set to correspond to the area R2a shown in FIG. 9, and the irradiation field 12d4' may be set to correspond to the area R2c shown in FIG. 9.

In the above-mentioned X-ray generator unit 90 shown in FIGS. 14 to 16, a plurality of slits having different heights in the direction in parallel to the axial direction of the rotary shaft 4a are used to be displaced relative to the X-ray source 9 in order to change the position of irradiation field. However, different techniques may be used, as shown in FIGS. 17A to 17C, 18A and 18B. Because they are modifications of the structure shown in FIG. 15(a), common items are not explained here. Further, in FIGS. 17A to 17C, a device for stopping rotation of the X-ray source 9 or a guide member are not explained because they can be realized with known mechanisms.

Figure 17A:
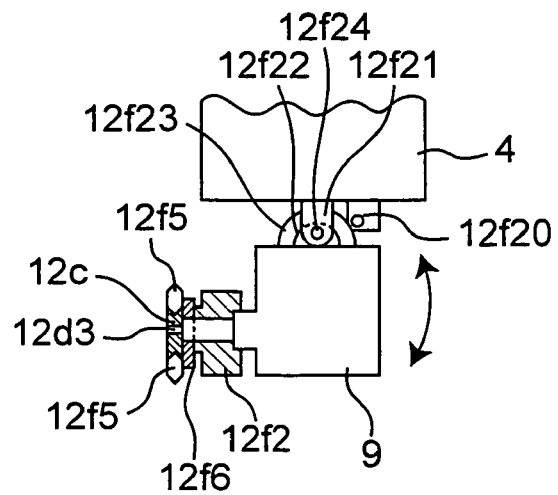
FIG. 17A is a further diagram for changing a position of an irradiation field.

FIG. 17A shows an embodiment of the X-ray generator unit 90 wherein the X-ray source 9 itself is rotated to change the irradiation field. In contrast to FIG. 15(a), the rotary arm (supporter) 4 is separated from the X-ray source 9, and the rotation members 12f22 and 12f21 are interposed between them. The rotation member 12f22 is mounted on the top of the X-ray source 9, and the other rotation member 12f21 is mounted on the bottom of the rotary arm 4 at a position in correspondence to the rotation member 12f22. The rotation members 12f21 and 12f22 are connected rotatably to a common rotary shaft 12f24. The axial direction of the rotary shaft 12f24 is set perpendicularly to a direction parallel to the axial direction of the rotary shaft 4a and perpendicularly to the direction of the X-ray beam B from the X-ray source 9 to the digital X-ray sensor 14. Therefore, the rotation member 12f22 can be rotated so that the X-ray beam from the X-ray source 9 to the digital X-ray sensor 14 is displaced in parallel to the axial direction of the rotary shaft 4a. At the top of the X-ray source 9, a fan-like member 12f23 is provided so that the pivot of the fan is fixed to the top of the X-ray source 9, and a motor 12f20 is mounted to the first attachment 30 of the rotary arm 4. The drive shaft of the motor 12f20 abuts to the arch-like periphery of the fan-like member 12f23 to rotate the fan-like member 12/23. The axial direction of the rotary shaft of the fan-like member 12/23 is set in the same direction as a rotary shaft 12/24. Therefore, when the motor 12/20 is driven, the X-ray source 9 is rotated, and the X-ray cone beam irradiated from the X-ray source 9 towards the digital X-ray sensor 14 is displaced in a direction parallel to the axial direction of the rotary shaft 4a.

Figure 17B:
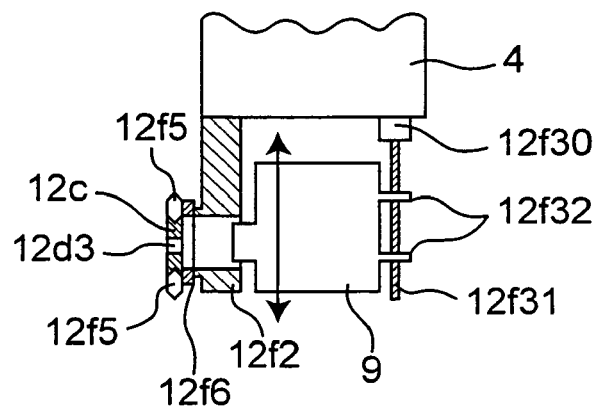
FIG. 17B is a still further diagram for changing a position of an irradiation field.

FIG. 17B shows an embodiment of the X-ray generator unit 90 wherein the X-ray source 9 itself is moved up and down relative to the slit plate 12c. In contrast to FIG. 15(a), the solid block 12/2 is fixed to the first attachment 30 of the rotary arm (supporter) 4. The X-ray source 9, is not fixed directly to the rotary shaft 4, and it can be moved up and down relative to the rotary arm 4 by the member 12/32 to be driven. A through hole provided in the solid block 12/2 to passes the X-ray beam from the X-ray source 9 is set to be moved up and down in a range relative to an end of the X-ray source 9. A motor 12/30 is fixed to the bottom of the first attachment 30 of the rotary shaft 4 so that a shaft of the motor 12/30 as a screwed shaft is extended downward. At the back plane of the X-ray source 9, members 12/31 to be driven are provided with screwed holes through which the shaft 12/31 are inserted so that the X-ray source 9 is moved up and down by the shaft 12/31. Thus, when the shaft 12/31 is driven, the X-ray source 9 is moved up and down relative to the solid block 12/2 and the slit 12d3 so as to change the irradiation field. That is, the X-ray beam irradiated by the X-ray source 9 to the digital X-ray sensor is shifted in a direction parallel to the axial direction of the rotary shaft 4a.

Figure 17C:
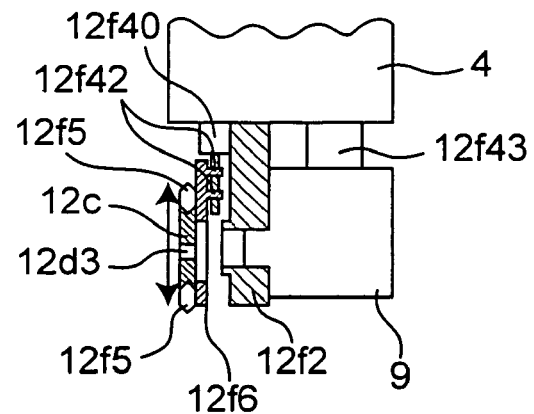
FIG. 17C is a yet further diagram for changing a position of an irradiation field.

FIG. 17C shows an embodiment of the X-ray generator unit 90 wherein the slit plate 12c is moved up and down relative to the X-ray source 9 to change the irradiation field. The X-ray source 9 is fixed to the first attachment 30 of the rotary shaft (supporter) 4, and the solid block 12/2 is fixed to the X-ray source 9. A motor 12/40 is fixed to the bottom of the first attachment 40 of the rotary shaft 4, extending its shaft 12/41 as a screwed shaft downward. In contrast to FIG. 15(a), the plate 12/6 for fixing rollers is separated from the solid block 12/2 and is moved up and down. Behind the plate 12/6, a member 12/42 to be driven is provided with screwed holes through which the shaft 12/41 of the motor is inserted. Therefore, when the shaft 12/41 is driven, the plate 12/6, the rollers 12/5 fixed to the plate 12/6 and the slit plate 12c interposed by the rollers are moved up and down so as to change the irradiation field. That is, according to the drive with the motor 12/40, the X-ray beam B irradiated by the X-ray source 9 towards the X-ray sensor 14 is displaced in a direction parallel to the axial direction of the rotary shaft 4a.

In FIGS. 17A to 17C, only the slit 12d3 is used for the areas R2a to R2c, and the other slits 12d2 and 12d4 may be omitted.

Figure 18A:
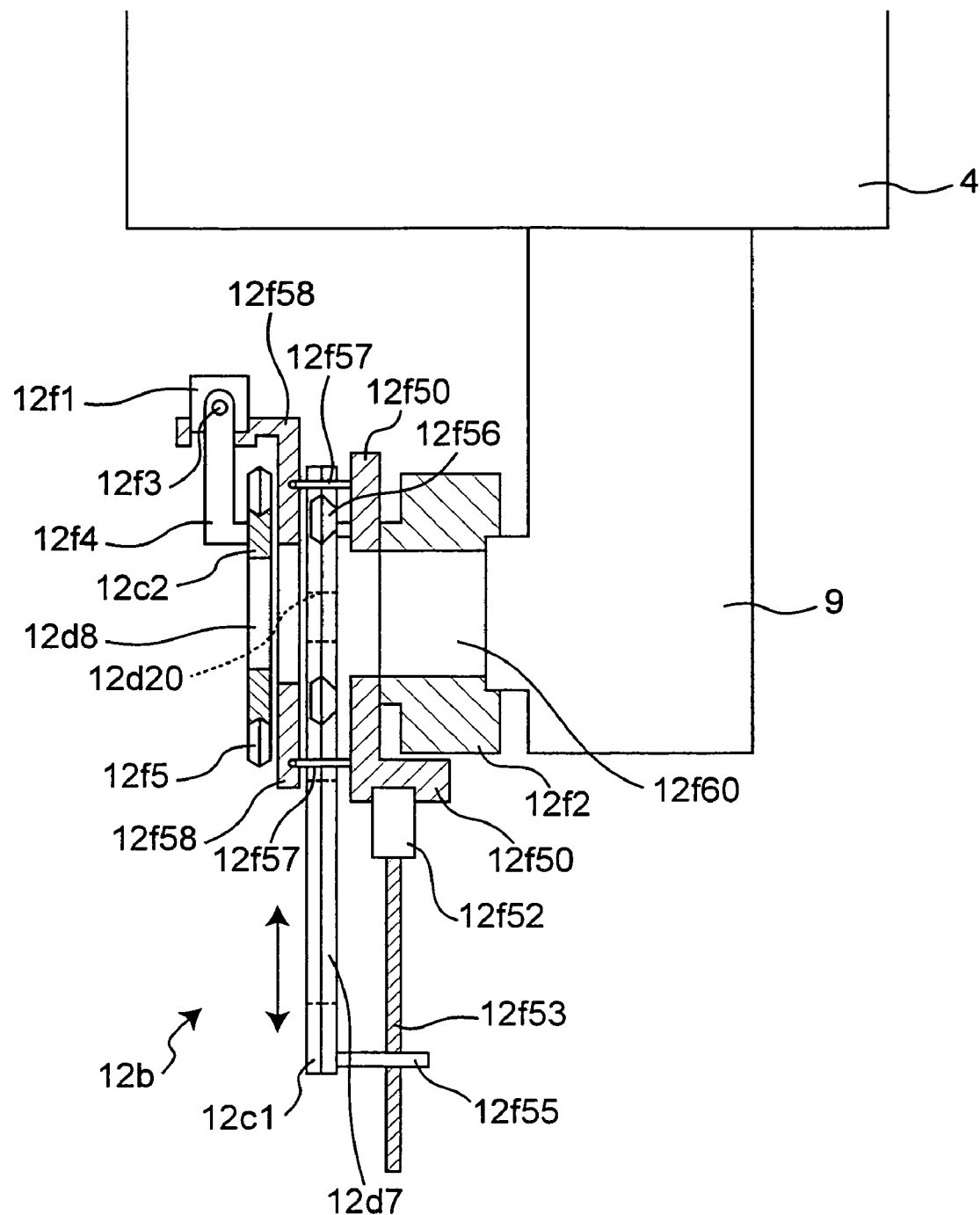
FIG. 18A is a side view for explaining a structure of a primary slit mechanism.
Figure 18B:
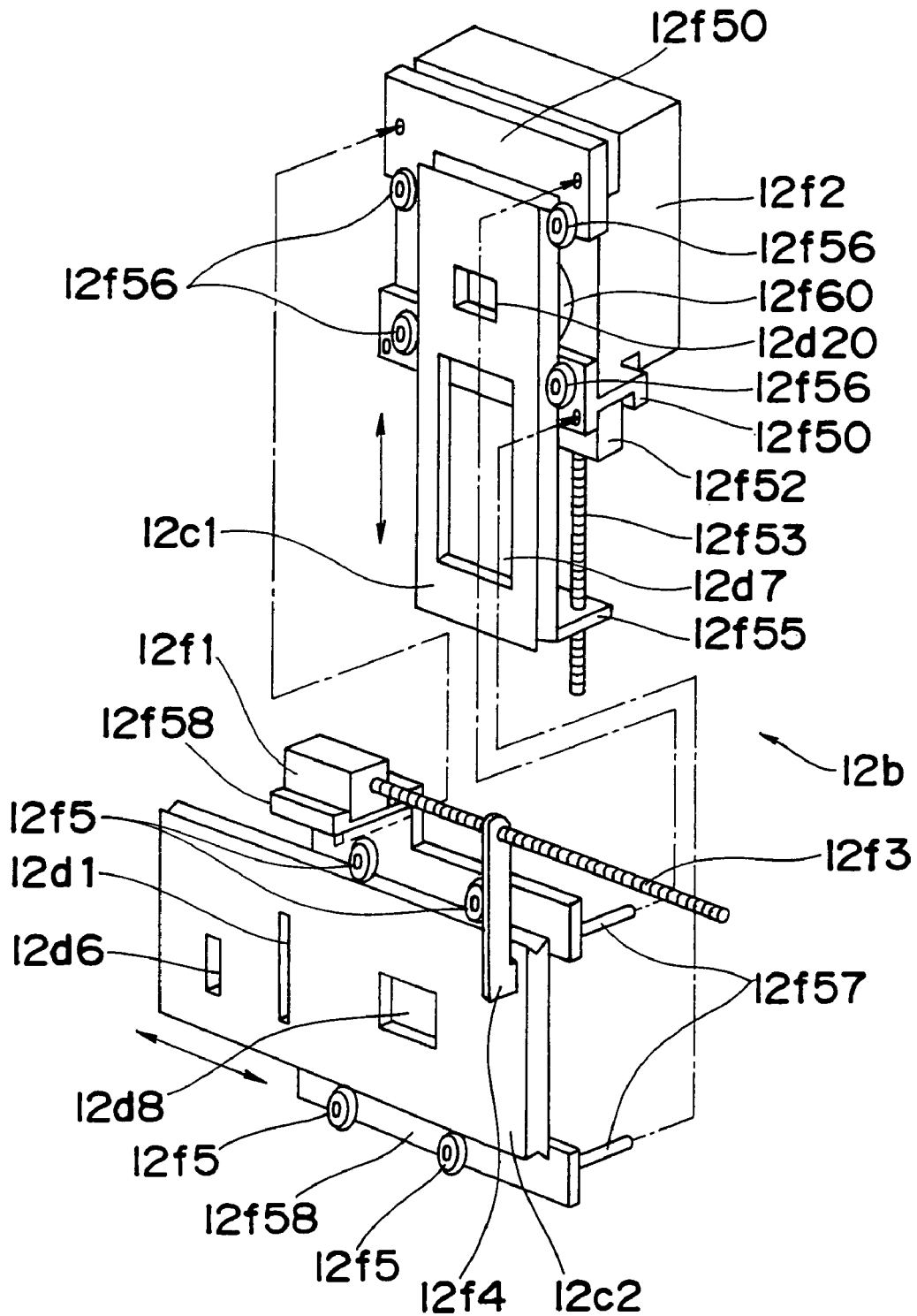
FIG. 18B is perspective view of a block mounted to an X-ray source and a mechanism provided in the block.

FIG. 18A is a side view for explaining a structure of the primary slit mechanism 12, and FIG. 18B is a perspective view of the solid block fixed to the X-ray source 9 and the mechanism for the solid block. In the explanation below, "front" designate a front in a direction of irradiation of the X-ray beam from the X-ray source 9. The X-ray source 9 is fixed to the rotary arm (supporter) 4, and the solid block fixed to the rotary arm 4 has a through hole through which the X-ray beam B from the X-ray source passes. Plates 12/50 for holding rollers above and below are fixed to the solid block 12/1 at the front so as not to prevent the passage of the X-ray beam B from the X-ray source 9. A motor 12/52 is fixed to the bottom of the plate 12/50 at the lower side so that a shaft 12/53 thereof as a screwed shaft extends downward. The slit plate 12c1 is guided by the four rollers 12/56 set to the plates 12/50 in a direction parallel to the axial direction of the rotary shaft 4a. The slit plate 12c1 has a slit 12d20 for regulating the X-ray beam B to the X-ray cone beam in correspondence to one of the areas R2a to R2c, and a large opening 12d7 provided for the above-mentioned purpose. Further, a member 12/55 to be driven and having a screwed hole is fixed to the slit plate 12c1 to be engaged with the shaft 12/53. By rotating the shaft 12/53, the slit plate 12c1 is driven along the axial direction of the shaft 12/53. Therefore, by driving the shaft 12/53, the slit plate 12c1 is displaced up and down in a direction parallel to the axial direction of the shaft 12/53.

Two plates 12/58 for holding the rollers are fixed to the front of the two plates 12/50 for holding the rollers with four pins 12/57 so as not to prevent movement of the slit plate 12c1 between the plates 12/58 and 12/50. The four rollers 12/5 are provided in front of the plates 12/58. At the top of the plate 12/58 at the upper side, a motor 12/1 is fixed so as to extend the shaft 12/3 as a screwed shaft laterally.

As shown in FIG. 18B, the slit plate 12c2 has the slit 12d1 longer in a direction parallel to the axial direction of the rotary shaft 4a in correspondence to the area R1. The slit 12d1 is provided for panoramic imaging and for linear scan imaging. Further the slit plate 12c2 has a large opening 12d8 for the above-mentioned purpose. A member 12/4 with a screwed hole is provided in front of the slit plate 12c2. The member 12/4 is engaged with the shaft 12/3 and is driven in the axial direction of the shaft 12/3 by rotating the shaft 12/3. Therefore, the slit plate 12c2 is displaced in a direction crossing the X-ray beam B by rotating the shaft 12/3. The rollers 12/5 guide the slit plate 12c2 according to the displacement.

A slit 12d6 for cephalometric imaging may be added further to the slit plate 12c2, as shown, similarly to slit plate 12c shown in FIGS. 14 to 16.

The slit 12d20 is used for CT imaging. In the case of CT imaging, the slit 12d20 is displaced by the motor 12/52 to a position to regulate the X-ray beam. By controlling the amount of displacement, the displacement of the slit 12d20 can be adjusted in a direction parallel to the axial direction of the rotary shaft 4a. In this case, the slit plate 12c2 is displaced by the motor 12/1 so as to bring the opening 12d8 in front of the slit 12d2. The opening 12d8 has a size so that the X-ray beam 12d8 passing through the slit 12d8 is allowed to pass. The size of the opening 12d8 is set to a value appropriate to the area R3 in the two-dimensional detection plane of the digital X-ray sensor 14. In this case, the opening 12d8 may also be used as a slit for the area R3, similarly to the slits 12d5 shown in FIGS. 14 to 16.

In the cases of panoramic imaging and linear scan imaging, the slit plate 12c2 is displaced by the motor 12/1 so the slit 12d1 regulates the X-ray beam B. At this time, the slit plate 12c1 is displaced by the motor 12/52 so that the opening 12d7 is behind the slit 12d1 without preventing the passage of X-ray beam B passing the slit 12d1.

The opening 12d7 is set to have a size so that the X-rays passing through the slit 12d1 and the opening 12d8 is allowed to pass. In the case of cephalometric imaging, the slit 12d1 is only replaced by the slit 12d6.

Figure 19:
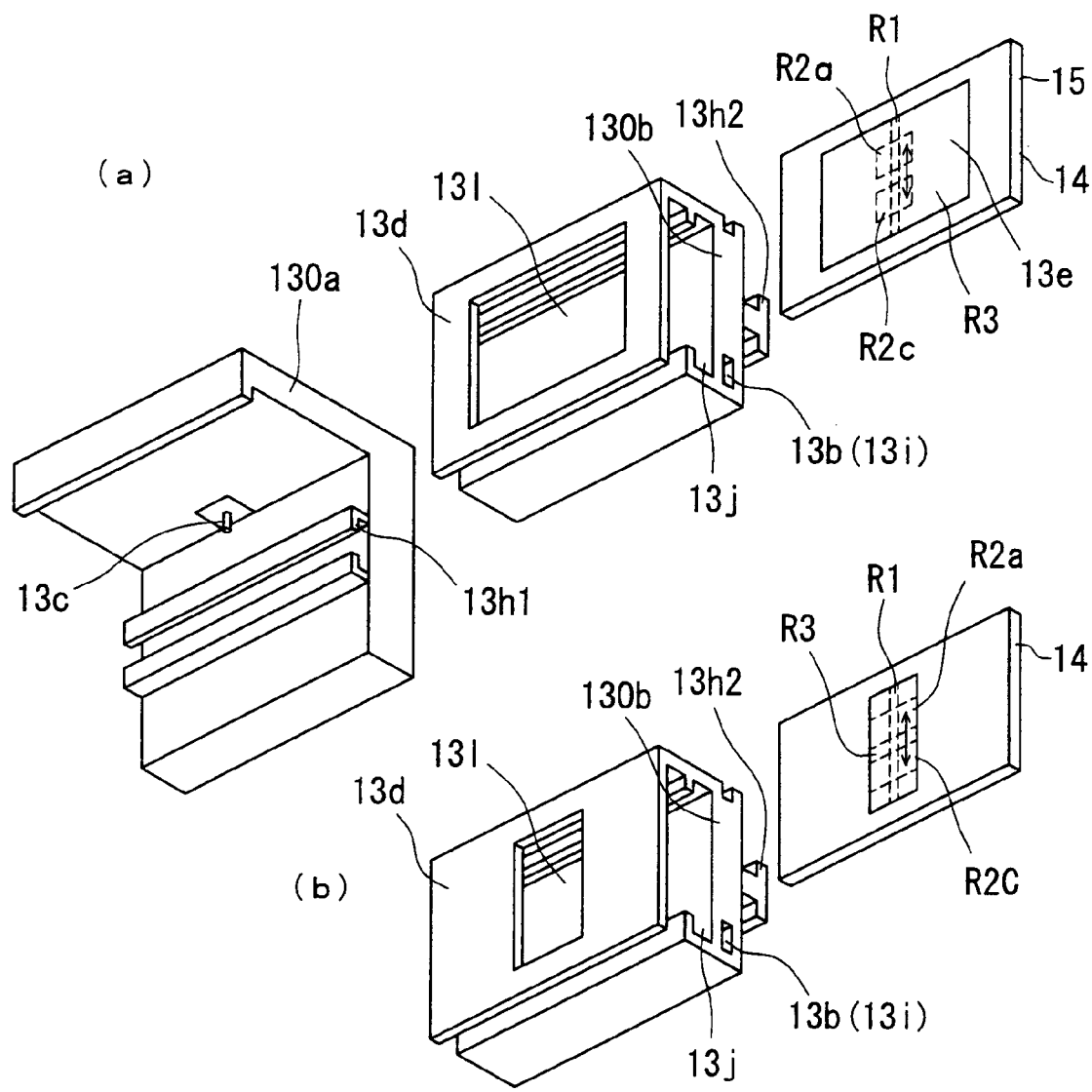
FIG. 19 is a diagram of an X-ray imaging unit.

FIG. 19(a) shows a basic structure of the X-ray imaging unit in the second attachment 31. The X-ray imaging unit 10 has a base 130a, a movable member 130b used as a sensor holder to be displaced in the base 130a in a direction parallel to the rotation direction of the X-ray imaging unit, and a cassette 15 used as a digital X-ray sensor 14 mounted to the movable member 130b. The cassette 15 has the two-dimensional detection plane 13e.

As explained above on FIG. 8, the two-dimensional plane 13e has the area R3 for CT imaging or for two-dimensional scout with a large irradiation field, the area R1 for panoramic imaging, and the areas R2a to R2c for CT imaging with a limited irradiation field. As to the area R2b not shown, refer to FIG. 8. As explained above, pixels to be read are controlled by the pattern generator 143. The irradiation field of the X-ray beam B can be changed by slits provided in the primary slit mechanism 12, and the entire area of the two-dimensional detection plane 13e may always be used as an effective area.

The movable member 130b has a member 13h2 to be guided. The base 130a has a guide 13h1 for guiding the member 13h2, and the movable member 130b is driven to be displaced, for example, by a cassette mover 13c having a motor and rollers. The movable member 130b has a receiver 13j for mounting a cassette 15 shown in the drawing. Further, it has a device 13d for limiting the irradiation field before the cassette 15 when the cassette is mounted. The device 13d has a flat plate and has an opening as a secondary slit 131 in correspondence to the size of the two-dimensional detection plane 13e, so as to allow irradiation of the X-ray beam towards the two-dimensional detection plane 13e while shielding unnecessary X-rays.

As shown in FIG. 19(b), the width of the area R3 may be set to the same width as the areas R2a to R2c in the digital X-ray sensor 14. As to the area R2b not shown, refer to FIG. 9. In FIGS. 19(a) and (b), the movable member 130b is an example of the cassette holder 10a shown in FIG. 2.

Figure 20:
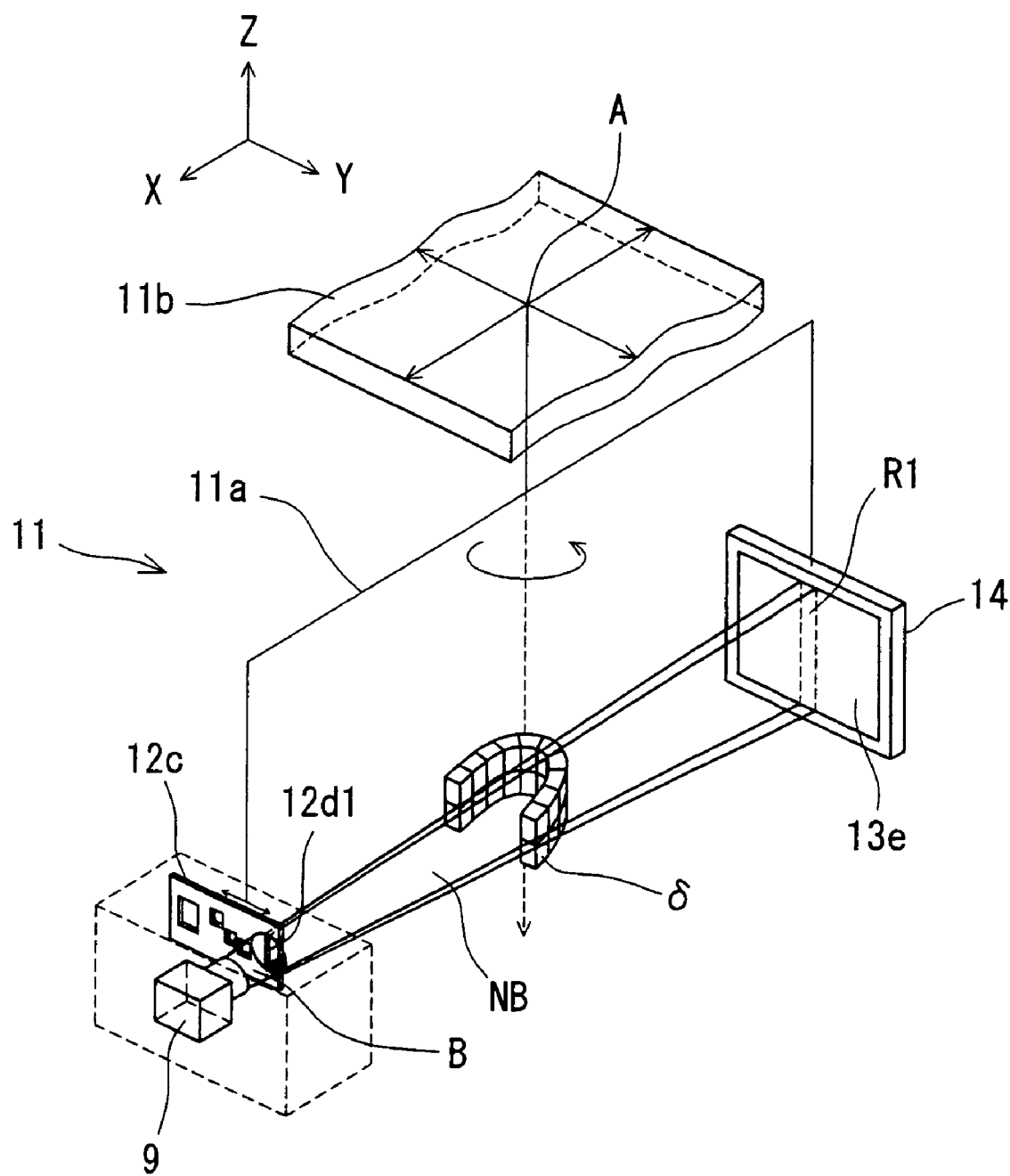
FIG. 20 is a schematic diagram for explaining panoramic imaging for a dental arch.

FIG. 20 shows schematically a state in panoramic imaging of a dental arch O. In the drawing, a line extended from the rotary shaft 4a passes a central part of the dental arch O. The X-ray beam B is regulated by the slit 12d1 in the slit plate 12c to become a long and narrow beam NB, and a narrow transmission image is projected to the area R1 in the two-dimensional detection plane 13e in the digital X-ray sensor 14. FIG. 20 is illustrated schematically for emphasis, simplification and the like. For example, the dental arch is shown in a larger size than the actual size.

As to the locus in panoramic imaging, refer to JP-B H02-18002 on a patent of the applicant on a panoramic X-ray radiography apparatus, wherein the locus of the movement of the rotation center of X-ray beam has an envelope locus of a general triangle symmetrical relative to a point protruding to the front teeth of dental arch. This embodiment may use such a locus for panoramic imaging.

Figure 21:
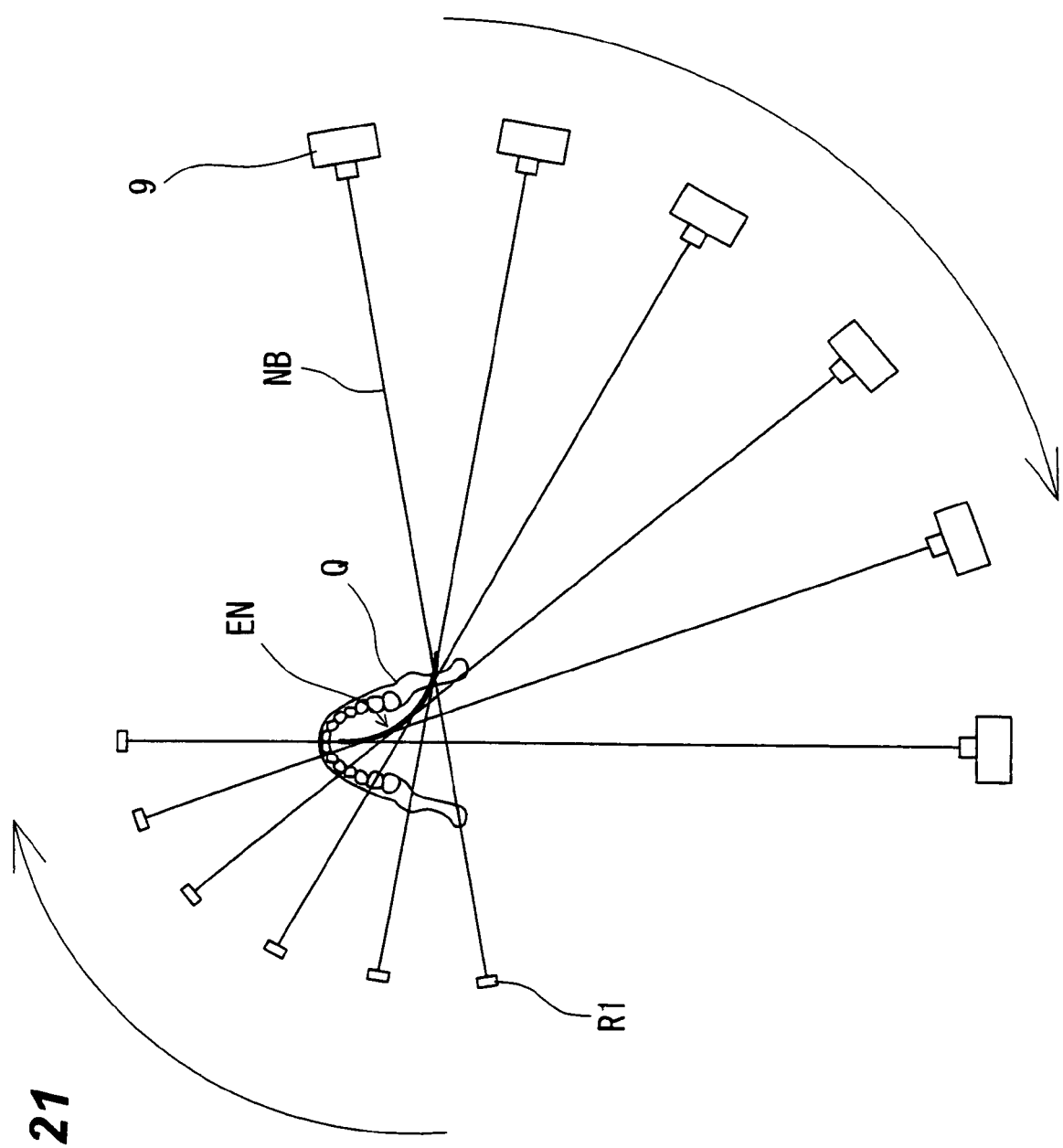
FIG. 21 is a diagram of loci of X-ray beam in panoramic imaging.

FIG. 21 shows an envelope EN of loci of the long and narrow beam NB irradiating from the X-ray source 9 towards the area R1 in the two-dimensional detection plane 13e of the digital X-ray sensor 14. FIG. 21 is a schematic view of the rotation of the X-ray source 9 and the digital X-ray sensor 14 around the dental arch O observed from above along the axial direction of the rotary shaft. As shown with an arrow, the X-ray source 9 and the digital X-ray sensor 14 are rotated clockwise.

Figure 22:
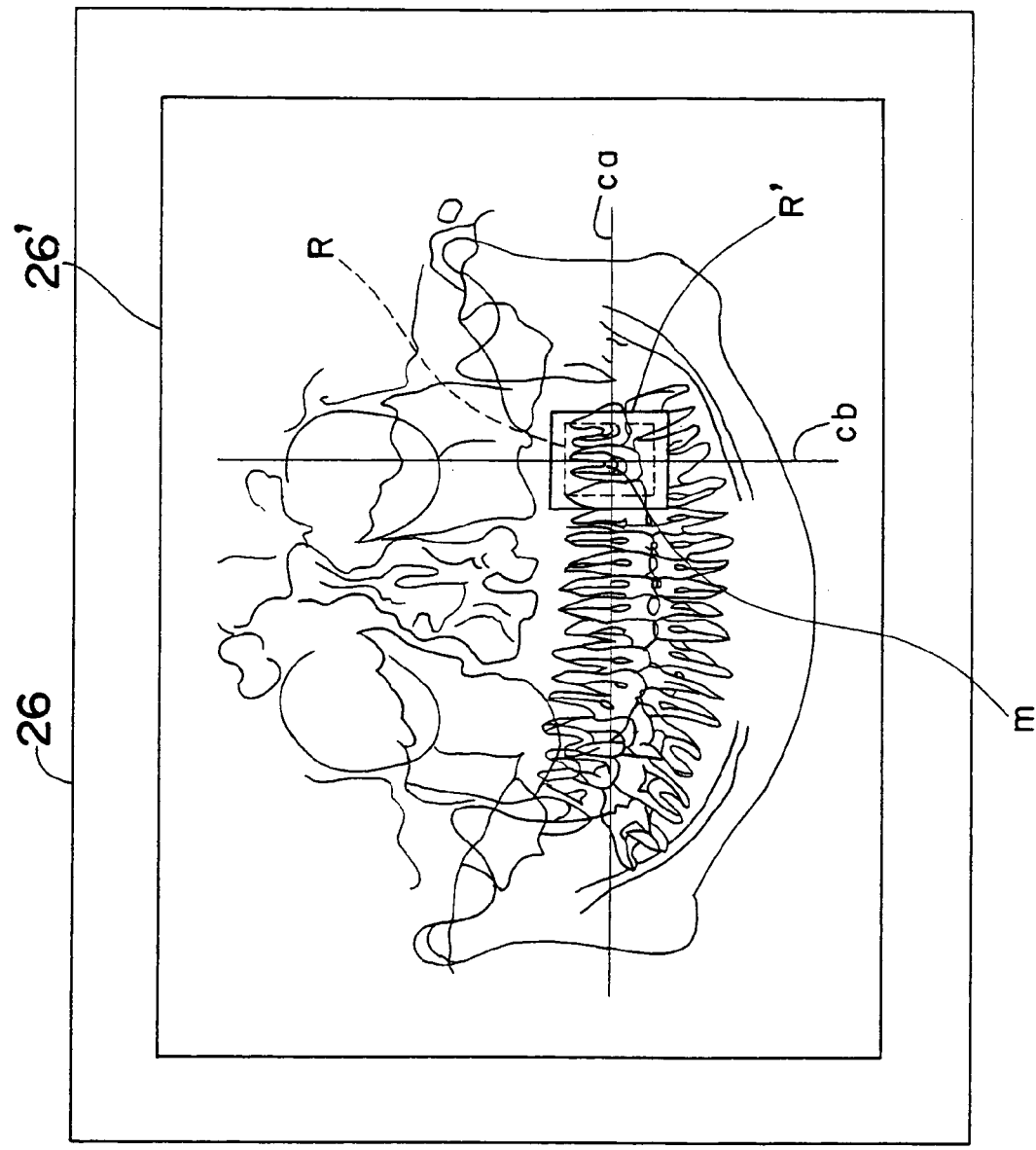
FIG. 22 is a diagram of an example of presentation of a panoramic image for setting an area of interest.

Next, CT imaging is explained using the position information on a region of interest which have been obtained by panoramic imaging. That is, when a region of interest R is designated in a panoramic image displayed based on panoramic imaging, the position of the designated region R is calculated, the area from which image data are read is changed, and the rotary arm is moved automatically. Then, CT imaging on the region of interest R is started as a second X-ray imaging. When a first X-ray image acquired by a first X-ray imaging (in this case panoramic imaging) is used to designate a region of interest and a second X-ray imaging (in this case CT imaging) is performed on the designated region of interest R, the first X-ray imaging is referred to as scout, a mode of performing the first X-ray imaging is referred to as scout mode, and acquisition of scout view based on panoramic imaging is referred to as panoramic scout. Panoramic imaging is performed first as the first X-ray imaging. After the panoramic imaging is completed, the acquired image data are processed for reconstruction, and a panoramic image as shown in FIG. 22 is displayed as a scout view in a screen 26' of the display apparatus 26. An operator designates a region of interest in the panoramic image with a cursor moved with to a mouse operation by a mouse not shown in the operation unit 17A and select CT imaging as the second X-ray imaging mode.

FIG. 22 shows an example of a panoramic image for designating a region of interest R. The designation of a region of interest R is performed with a cursor moving in the screen 26' of the display device 26 according to an operation with the operation unit 17A. Any cursor may be used such as an arrow cursor, a crossing cursor, a rectangular cursor representing a border of the region of interest, or any combination thereof. Cursors "ca" and "cb" are examples of a crossing cursor. In this case, the cursors "ca" and "cb" operated with a mouse or the like are moved in the screen to designate a region of interest R. A crossing point of the cursors "ca" and "cb" is defined as a target point "m" in a region of interest R, and the three-dimensional position of the target point "m" in the region of interest is determined with the cursors "ca" and "cb" by an operator. The cursors "ca" and "cb" may be fixed with clicking in images Sc1, Sc2. The two cursors may be moved simultaneously by holding and moving the crossing point thereof.

The cursor R' shown with a dashed line is an example of a rectangular cursor. By referring to two diagonals between four vertexes of the rectangle shown with the cursor R', the center of a region of interest R is designated at the crossing point of the two diagonals. It is also possible to display a cursor R' having the size and shape of the region of interest R. The cursors "ca" and "cb" and the cursor R' may be displayed at the same time.

The three-dimensional position of the region of interest or the target point "m" may be designated explicitly in a panoramic image with the two coordinate axes. Further, the position may be calculated automatically based on the locus of the X-ray beam on panoramic imaging, with respect to the thickness direction of a panoramic image.

After the designation of the three-dimensional position of a target point "m" is completed as explained above, at least one of the mechanism including the XY table for moving horizontally, the up-and-down frame 11 and an object holder not shown is adjusted so that the rotary shaft 4a of the rotary arm (supporter) 4 is set to the target position "m". Thus, the position of the rotary arm 4 and/or the object holder is controlled so that the target point "m" is aligned to an extension of the rotary shaft 4a. Next, the X-ray source 9 and the digital X-ray sensor 14 are rotated around the rotary shaft 4a for CT imaging, and a CT image of the region of interest R is acquired.

Figure 23:
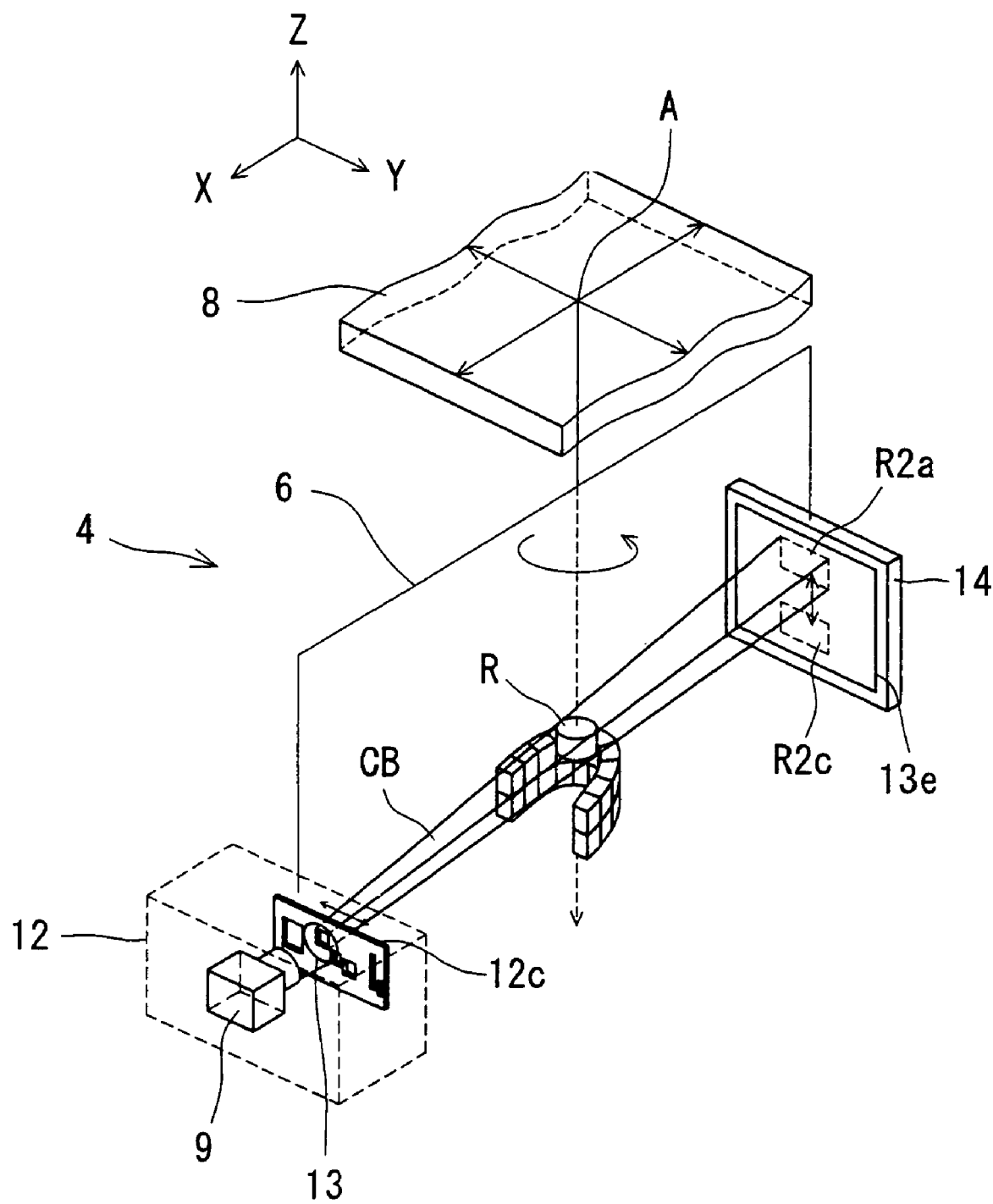
FIG. 23 is a schematic diagram of computed tomography scanning in an area of interest.

FIG. 23 shows a situation of CT imaging on a region of interest R schematically wherein the CT imaging is performed with a limited irradiation field. An extension of the rotary shaft 4a passes through the center of a cylindrical region of interest R. The X-ray beam B is regulated by the slit 12d2 in the slit plate 12c, and a transmission image including the entire region of interest R is projected towards the area R2a in the two-dimensional detection plane 13e of the digital X-ray sensor 14. The X-ray source 9 and the digital X-ray sensor 14 are moved synchronously along the rotation locus around the rotary shaft 4a as the center of the optical system.

Figure 24:
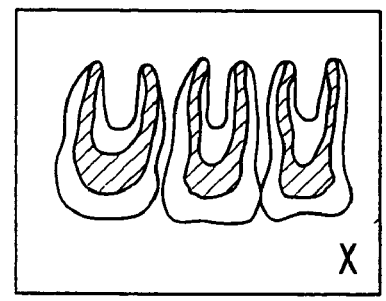
FIG. 24 is a diagram of presentation of a CT image.
Figure 24:
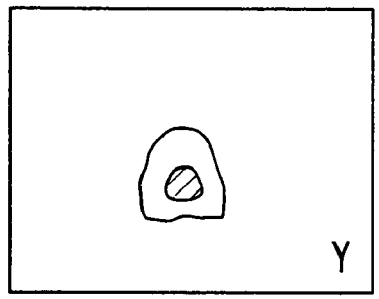
Figure 24:
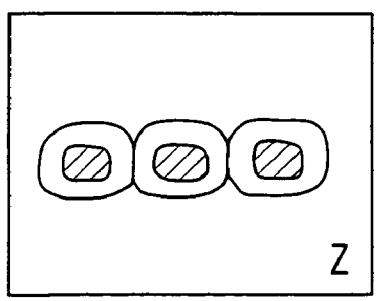
Figure 24:
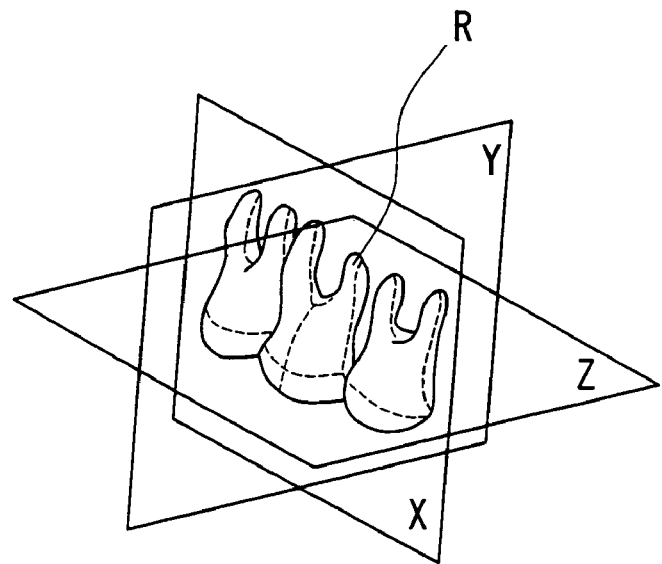

FIG. 24 shows an example of a CT image displayed with the display apparatus 26 after transmission images on a region of interest are taken, wherein X, Y and Z directions are perpendicular to each other. The Z direction is set to agree with the rotary shaft 4a, but it may be set at any angle. The X, Y and Z planes represent planes perpendicular to the X, Y and Z directions, and tomogram images in the X, Y and Z planes are displayed. These planes are sections in the region of interest R, and images in the sections are displayed. The region of interest R may be rotated or moved relative to the sections perpendicular to each other as desired, and tomogram images corresponding to the rotation and the movement can be reconstructed based on the transmission images acquired in CT imaging.

Figure 25:
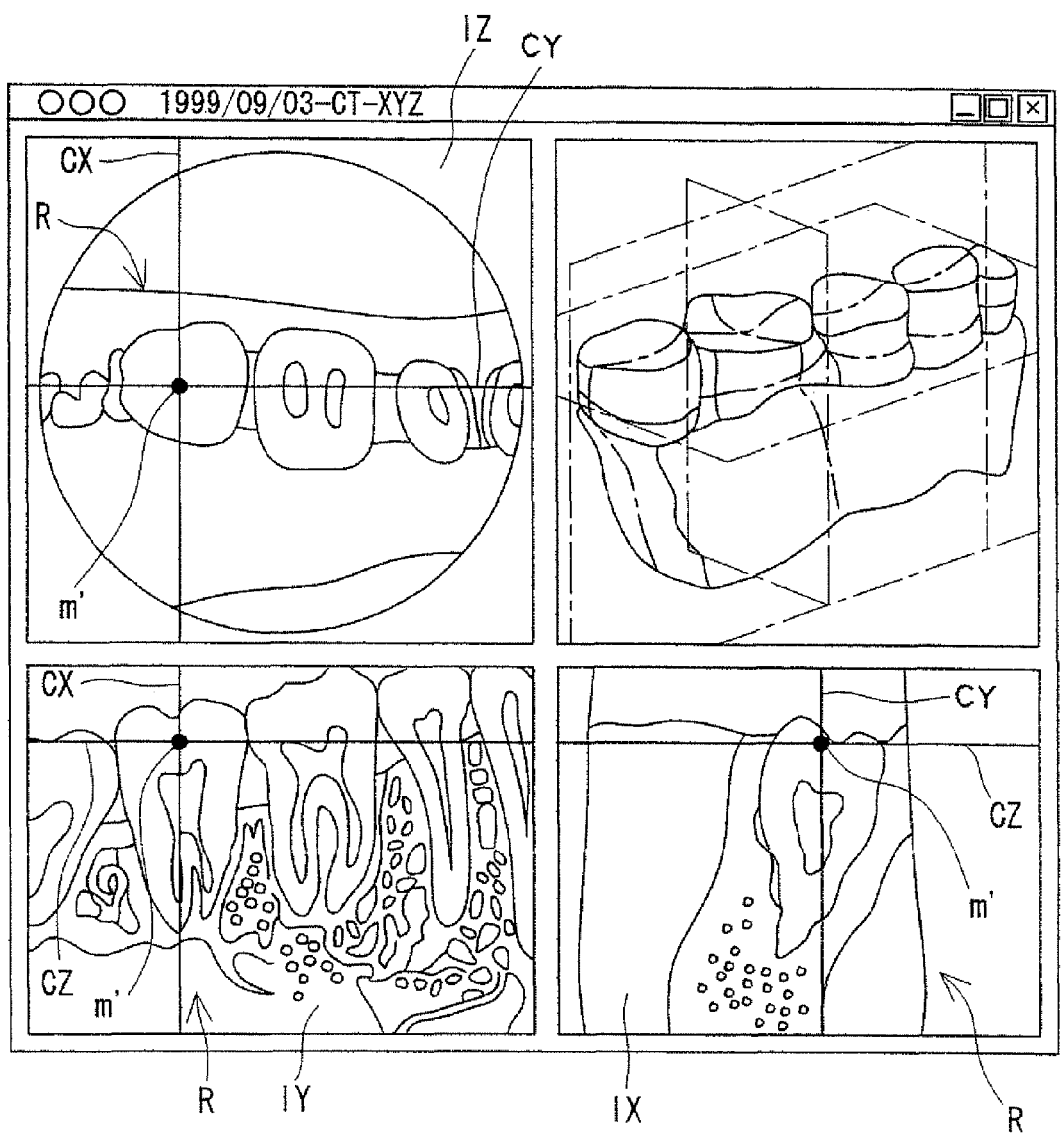
FIG. 25 is a more detailed diagram of presentation of a CT image.

FIG. 25 shows an example of the tomogram images shown in FIG. 24 in detail. The region of interest R in FIG. 25 is different from that shown in FIG. 24. In FIG. 25, IX, IY and IZ denote tomogram images in an X plane, in a Y plane and in a Z plane, respectively, of the region of interest R shown in the screen 26' of the display device 26. Further, CX, CY and CZ denote X, Y and Z cursor, respectively, representing projection to the other planes. The X, Y and Z planes are designated for representing the tomogram images IX, IY and IZ. The X cursor CX is displayed in the Y and Z tomogram images IY, IZ as a projection of X plane; the Y cursor CY is displayed in the Z and X tomogram images IZ, IX as a projection of Y plane; the Z cursor CX is displayed in the X and Y tomogram images IX, IY as a projection of Z plane. That is, the X cursor CX shown in the Y tomogram image IY and the Z tomogram image IZ represents the position of X plane; the Y cursor CY shown in the Z tomogram image IZ and the X tomogram image IX represents the position of Y plane; and the Z cursor CZ shown in the X tomogram image 1x and the Y tomogram image IY represents the position of Z plane.

A point "m'" denotes any point in the region of interest R. In FIG. 25, tomogram images including the point "m'" are presented. The point "m'" may be set to the target point "m" designated in the panoramic scout in the initial stage wherein the tomogram images IX, IY and IZ are presented. That is, when the target point "m" is designated in the scout, and images acquired in CT imaging are displayed, the tomogram images IX, IY and IZ including the target point "m" are presented. Thus, the target point "m" is displayed at the point "m'". Then, as the cursor is moved, the point "m'" is moved to a point different from the target point "m".

In FIGS. 24 and 25, the tomogram images IX, IY and IZ are presented as a conventional arrangement of a plan view, a front view and a side view. Thus, tomogram images when the point "m'" is observed in the three directions are presented. Therefore, the relative relationship between the three tomogram images IX, IY and IZ can be understood intuitively.

As explained above, the area R1 longer in a direction parallel to the rotary shaft 4a of the rotary arm (supporter) 4 is set, or one of the areas R2a to R2c for CT imaging is set in the two-dimensional detection plane 13e of the digital X-ray sensor 14. Then, the shape of the X-ray beam B is changed according to each of the areas R1 and R2a to R2c. The primary slit mechanism 12 is provided for the X-ray generation unit 90 as a device for changing the irradiation field at least in a direction parallel to the axial direction of the rotary shaft 4a.

Then, a first X-ray image acquired in the area R1 is presented by the display device 26, and a region of interest R is designated with an operation device of the operation unit 17A in a panoramic image as the first X-ray image. Next, the primary slit mechanism 12 is controlled to acquire a second X-ray image as a CT image of the designated region of interest R.

Embodiments explained above use a panoramic image for scout views. Alternatively, transmission images acquired in a plurality of directions may be used for scout views.

Next, two-directional scout is explained. Two-dimensional scout denotes to acquire transmission images in a plurality of directions to acquire a scout view. It is preferable to acquire transmission images in two directions in order to reduce the dose of X-rays. The acquisition of transmission images may be acquired in three or more directions. In this description, the latter case is also included in the term of two-dimensional scout.

In CT imaging explained below, position information on the region of interest obtained with two-directional scout from the transmission images in a plurality of directions is used. First, transmission images in a plurality of directions are acquired as the first X-ray imaging, and they are displayed as a scout view. Next, a region of interest is designated in the transmission images displayed, the position of the designated region of interest R is calculated, and CT imaging is performed as a second X-ray imaging on the region of interest R. A region to be read may be changed. Thus, when a region of interest is designated in the transmission images in a plurality of directions, the rotary arm is moved automatically for CT imaging on the region of interest.

Figure 26:
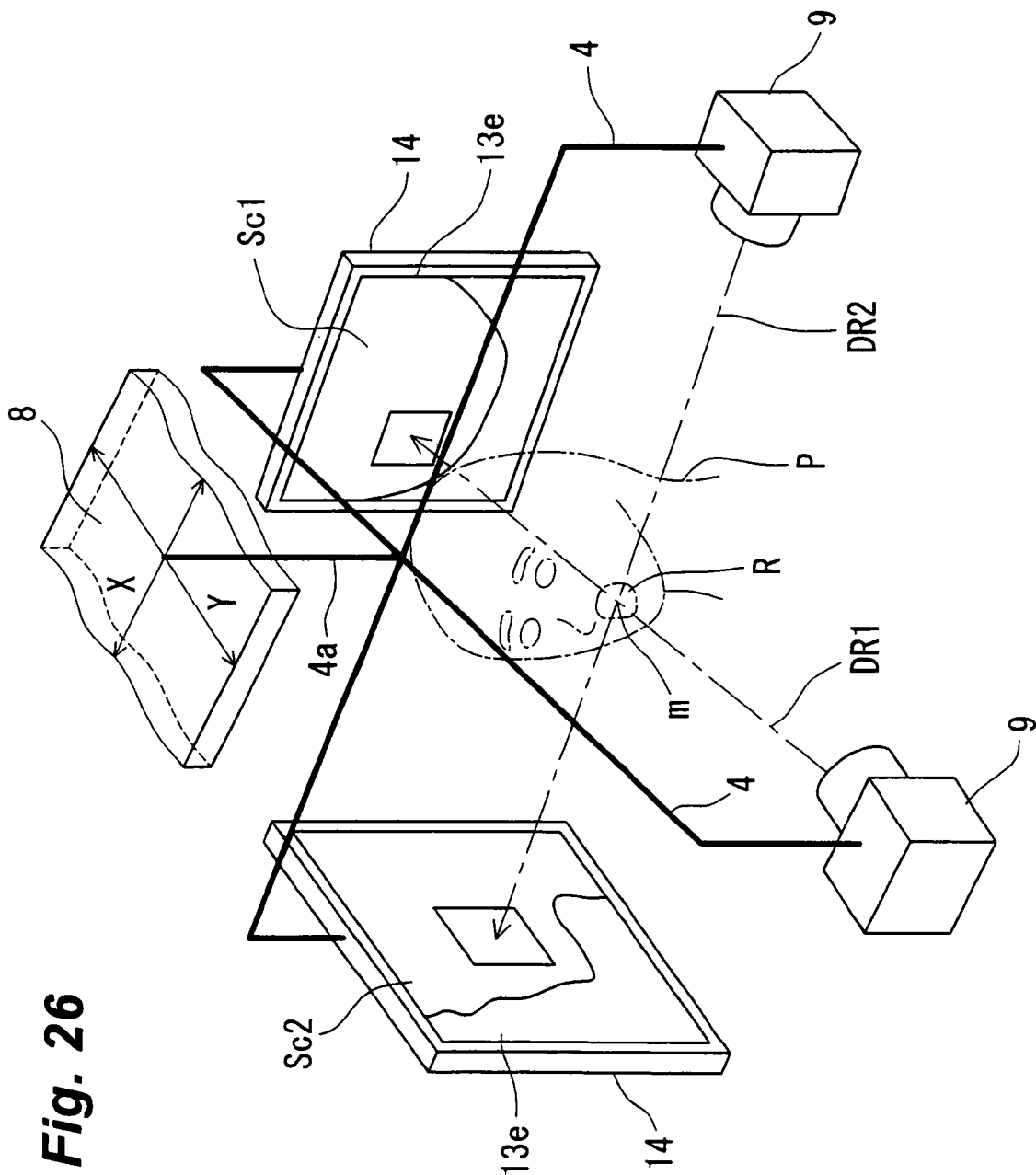
FIG. 26 is a diagram of presentation of two-directional scouting.

The two-dimensional scout is explained further. As shown in FIG. 26, the position of the rotary arm (supporter) 4, that of the object holder such as a chair and the like are controlled and the object, the X-ray source 9 and the digital X-ray sensor 14 are positioned broadly. In concrete, the head of a person as the object is positioned between the X-ray source 9 and the two-dimensional detection plane of the digital X-ray sensor 14. Then, the three components, that is, the object, the X-ray source 9 and the two-dimensional detection plane 13e of the digital X-ray sensor 14 are positioned so as to satisfy a first position relationship, for example, an arrangement wherein the X-ray beam transmits from the front to the rear of the head or in a direction DR1. A first transmission image (hereinafter referred to scout image) Sc1 is acquired in the position relationship. Next, the rotary arm 4 is rotated by an appropriate angle (for example, 90 degrees) to set the three components in a second position relationship, for example, an arrangement wherein the X-ray beam transmits from the left side to the right side of the head or in a direction DR2. A second scout image Sc2 is acquired in the position relationship. The first and second scout images Sc1 and Sc2 are stored in the video memory 24. The imaging of the two images is performed by using the operation unit 17A.

In the two-directional scout, the area R3 is set in the two-dimensional plane 13e in the digital X-ray sensor 14, to read image data in a wide area. Then, the slit 12d5 is selected in the primary slit mechanism in correspondence to the area R3.

Figure 27:
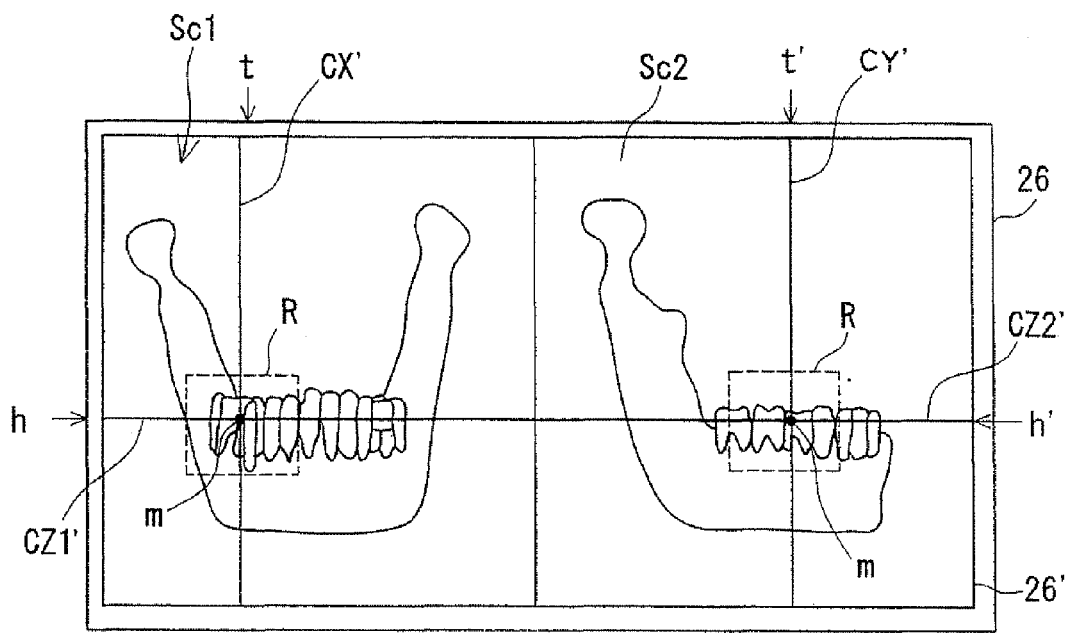
FIG. 27 is a diagram of presentation of scout image.

As shown in FIG. 27, the scout images Sc1 and Sc2 are displayed at the left and right sides in a screen. In the scout images Sc1 and Sc2, only the dental arch and the jaw joint are drawn for the easy understanding. For example, in the first scout image Sc1 shown at the left side, a pointer is operated with a mouse or the like to move the cursor CX' to the center in the region of interest in horizontal direction so as to designate a position "t" in the horizontal direction. Next, the cursor CY' is moved to the center in the region of interest in vertical direction so as to designate a position "h" in the vertical direction. Thus, the cursor CY' representing the position "t'" is located in the second scout image Sc2 at the center as a default position, and the cursor CZ' representing the position "h" is located in the first scout image Sc1 as a default position. Next, the pointer is moved to the second scout image Sc2, and the pointer is operated to move the cursor CY' to the center of the region of interest R in the horizontal direction to designate the position "t'" in the horizontal direction. The cursor CZ1' representing the position "h" in the first scout image Sc1 and the cursor CZ2' representing the position "t'" in the second scout image Sc2 are common elements in the two images, and they are presented at the same time. The cursor CZ1' may be related to the cursor CZ2'. That is, when one of the cursors CZ1' and CZ2' is moved, the other is also moved automatically to the corresponding position. The cursors CX', CY' and CZ1 (CZ2) may be confirmed by a click in the first and second scout images. By moving a crossing point of two of the cursors CX', CY' and CZ1 (CZ2), the relevant two cursors may be moved at the same time. A rectangular cursor may be used similarly to the rectangular cursor R' in the panoramic scout explained above. Based on the designation with the cursors, the three-dimensional position of a target point "m" in the region of interest R can be determined by an operator.

After the designation of the three-dimensional position of the target point "m" is completed as explained above, the position of at least one of the mechanism for moving in a horizontal plane including the XY table, the up-and-down frame 11 and the object holder (not shown) is controlled so that the rotary shaft 4a of the rotary arm is positioned at the target point "m" calculated by the CPU 19. After the position control of the rotary arm 4 and/or the object holder to position the target point "m" in a line extending from the rotary shaft 4a, the X-ray source 9 and the digital X-ray sensor 14 are rotated around the rotary shaft 4a for CT imaging, to acquire a CT image on the region of interest.

Figure 28:
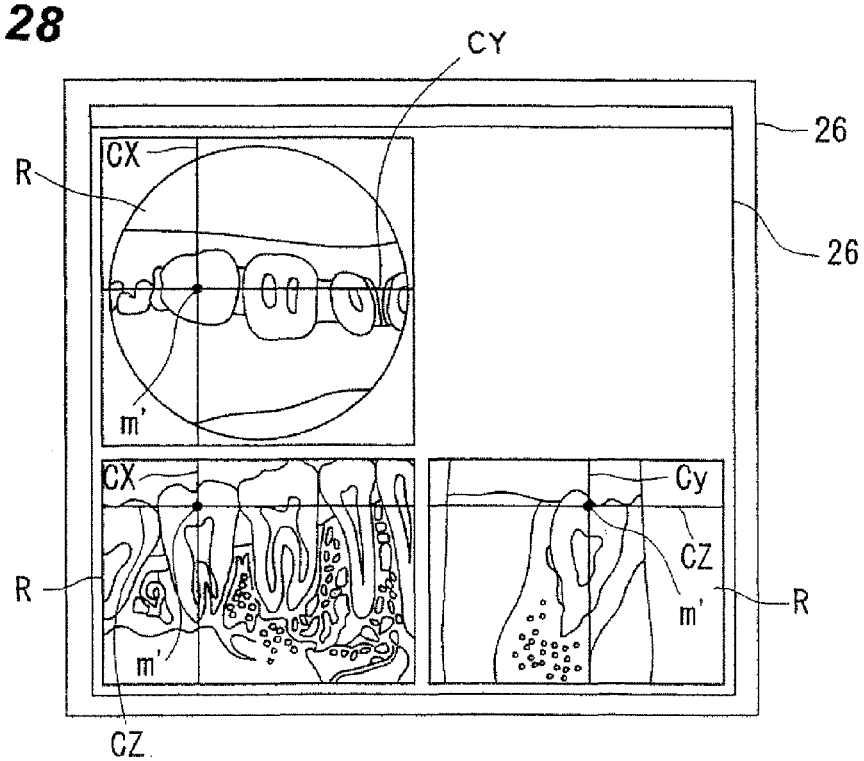
FIG. 28 is a diagram of presentation of a CT image.

FIG. 28 shows an example of presentation of an obtained CT image. The presentation of a CT image is not explained in detail because it is similar to that explained on FIG. 25.

As explained above, two-dimensional scout for shooting an object is performed in a plurality of position conditions different on the position relationship between the X-ray source 9, the object and the two dimensional detection plane 13e of the digital X-ray sensor 14. Next, the two-dimensional position data of the target point "m" determined in transmission images obtained with the two-dimensional scout is operated to determine the three dimensional position of the target point "m". Then, the rotation center of the X-ray source 9, the object and the two-dimensional detection plane 13e of the digital X-ray sensor 14 is controlled to come to the three-dimensional point, or the three dimensional point is controlled to come to the extension of the rotary shaft 4a of the rotary arm (supporter) 4. Thus, the region of interest R is subjected to CT imaging to acquire CT images. As to the structure for the two-directional scout, refer to JP-A 2004-329293 of the applicant.

Figure 29:
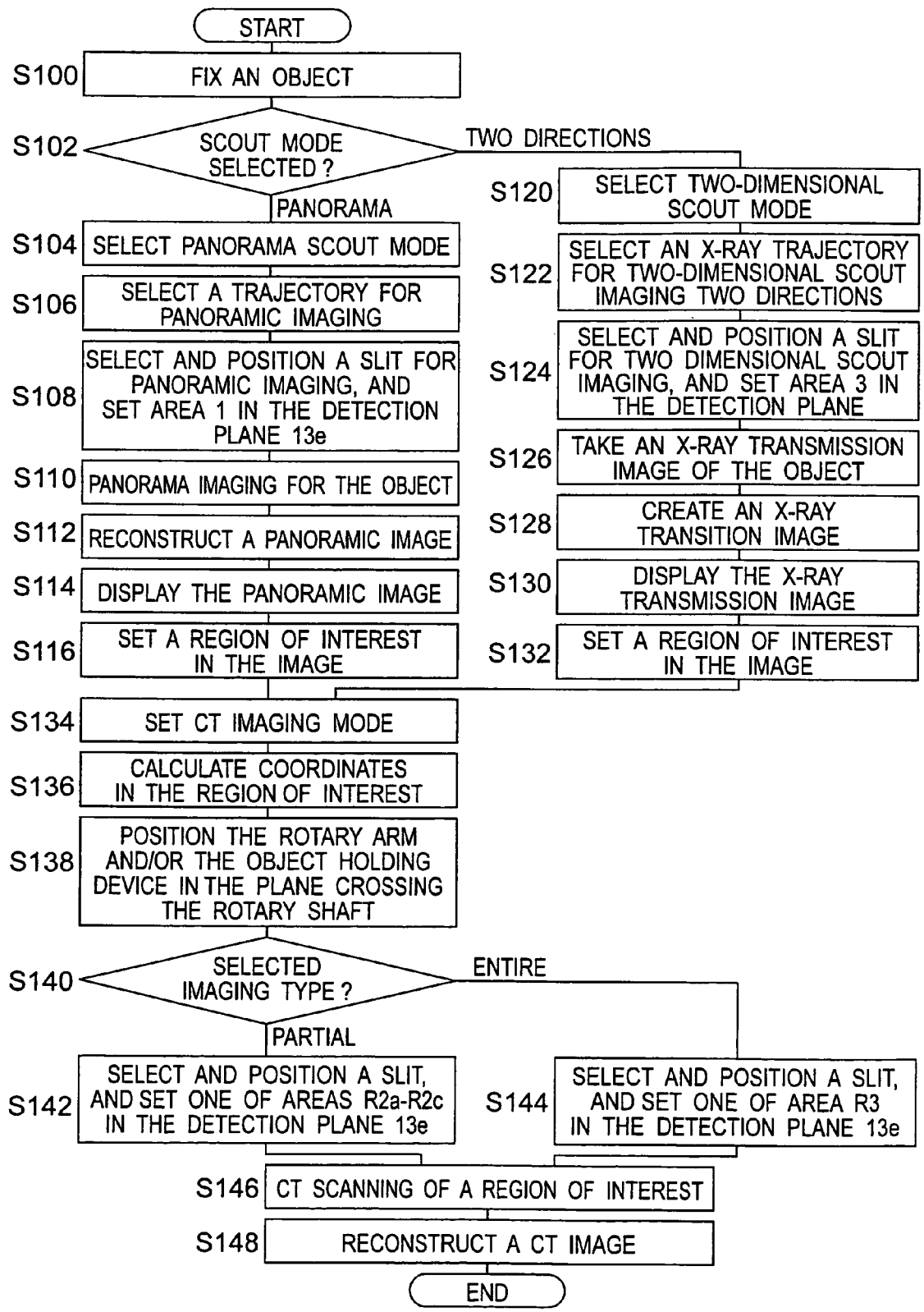
FIG. 29 is a flowchart of control by a central processing unit.

FIG. 29 shows a flowchart of the control of imaging by the CPU 19. First, an object is set and fixed to a reference position (or at the device for holding the object) (S100).

Next, a mode selection by an operator for the first X-ray imaging between panoramic scout or two-dimensional scout is received from the operation unit 17A (S102), and the flow branches according to the mode selection.

When panoramic scout mode is selected by the operator, it is set (S104), and a locus for panoramic imaging is selected as a locus of the X-ray beam (S106). Further, in the embodiments shown in FIGS. 14, 15 and 16, the slit 12d1 is selected and positioned for panoramic imaging, or in the embodiment shown in FIGS. 18A and 18B, the slit 12d1 is selected and adjusted on the position in the horizontal direction, and the vertical position of the opening 12d7 is adjusted to be positioned behind the slit 12d1, and the area R1 is set in the two-dimensional detection plane 13e of the digital X-ray sensor 14 (S108). Then, the movement of the rotary arm (supporter) 4 is controlled according the selected locus for panoramic imaging to perform panoramic imaging (S110).

Next, a panoramic image is reconstructed based on the panoramic imaging and is displayed with the display device 26 (S112 and S114). Next, when the operator designates a region of interest R or more precisely a target region "m" in the region of interest R by moving a cursor with a mouse on the displayed panoramic image, the designation is inputted (S116).

On the other hand, when two-dimensional scout mode is selected by the operator, it is set (S120), and a locus for two-directional scout imaging is selected as a locus of the X-ray beam (S122). Further, in the embodiments shown in FIGS. 14, 15 and 16, the slit 12d5 for two-directional scout is selected and positioned, or in the embodiment shown in FIGS. 18A and 18B, the slit 12d8 is selected and adjusted on the position in the lateral direction, and the vertical position of the opening 12d7 is adjusted to be positioned behind the slit 12d8, and the area R3 is set in the two-directional detection plane 13e of the digital X-ray sensor 14 (124). Then, the movement of the rotary arm (supporter) 4 is controlled according the selected locus for two-directional scout to perform two-directional scout imaging (S126). Next, a plurality of transmission images are created based on the two-dimensional scout, and they are displayed with the display device 26 (S128 and S130). Next, when the operator designates a region of interest R or more precisely a target region "m" in the region of interest R in the displayed transmission images by moving a cursor with a mouse on the displayed images, the designation is inputted (S132).

Next, CT mode is set as a first X-ray imaging mode (S134). Coordinate calculation is performed in the designated region of interest R, or more precisely in the target region "m" in the region of interest R (S136). Then, the rotary arm (supporter) and/or the device for holding an object is positioned in a flat plane intersecting the rotary shaft 4a (S138).

As to CT imaging, one of two modes can be selected. In one mode an X-ray cone beam in a small irradiation field CB is generated, and data are read from one of areas R2a to R2c as a part of the two-dimensional detection plane 13e of the digital X-ray sensor 14. In the other mode an X-ray cone beam in a large irradiation field CB is generated, and data are read from the entire area R3 in the two-dimensional detection plane 13e. When an operator selects a mode with the operation unit 17A, the selection is inputted (step S140), and the flow branches according to the selection.

When the imaging for reading from one the areas R2a to R2c is selected in the embodiments shown in FIGS. 14 to 16, one of the slits 12d2 to 12d4 is selected and positioned according to the height of a region of interest R, while in the embodiments shown in FIGS. 18A and 18B, the slit 12d20 is selected and the vertical position is adjusted and positioned, and the lateral position is adjusted and positioned so that the opening 12d8 is located before the slit 12d20 (step S142).

On the other hand, in the embodiments shown in FIGS. 14 to 16, when an imaging for reading data from the area R3 is selected, the slit 12d5 is selected. On the other hand, in the embodiments shown in FIGS. 18A and 18B, the opening 12d8 is selected, it is adjusted and positioned on the position in the vertical direction, and it is adjusted on its vertical position so that the opening 12d7 is put behind the opening 12d8 (step S144).

Next, the CT imaging is performed on the region of interest based on the settings (step S146), and CT images are reconstructed based on the data (step S146).

Figure 30:
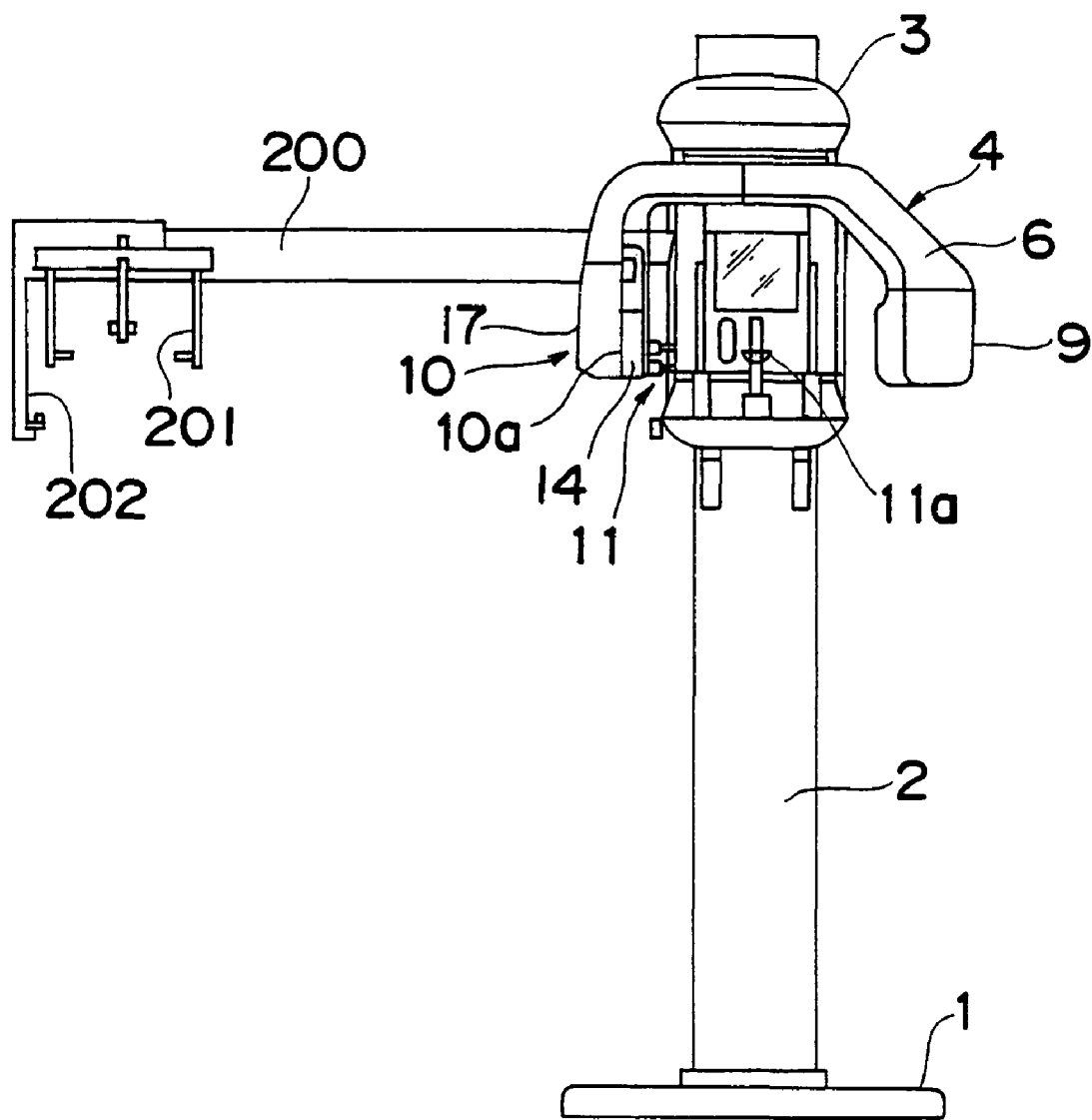
FIG. 30 is a front view of an X-ray imaging apparatus wherein a cephalometric imaging is provided.

FIG. 30 shows an X-ray imaging apparatus with which cephalometric imaging is available besides panoramic imaging. The X-ray imaging apparatus has a basic structure similar to the X-ray imaging apparatus shown in FIG. 1, but it is different in that an arm 200 for cephalometric imaging, a device 201 for fixing a head for cephalometric imaging and a cassette holder 202 are added. The arm is supported behind the up-and-down frame 11, and it is long towards the left side in the drawing. The cassette holder 202 is provided at a side opposite to the arm 200 with respect to the X-ray imaging apparatus. The cassette holder 202 can be displaced in a direction from the front to the rear and vice versa relative to the head holder 201, with a drive mechanism not shown.

The digital X-ray sensors 14 shown in FIGS. 10(a) to (c) may be set detachably in the cassette holder 202 or 10a. Further, in the case of cephalometric imaging, one of the digital X-ray sensors 14 shown in FIGS. 10(a) to (c) may be set to the cassette holder 202. Further, in the cases of panoramic imaging and CT imaging, one of the digital X-ray sensors 14 shown in FIGS. 10(a) to (c) may be set to the cassette holder 10a.

As to the digital X-ray sensor shown in FIG. 10(a), it is not needed to drive the cassette holder 202, and it is only fixed to the cassette holder 202 for cephalometric imaging. Further, a drive mechanism (not shown) in the cassette holder may be omitted.

Apparatuses for cephalometric imaging with a digital X-ray sensor are described in JP-A 2002-245277 and JP-A 2003-245177 of applications of the applicant, and the structures thereof may be used for this invention. In an apparatus shown in JP-A 2002-17718, the length of the two-dimensional detection plane of the digital X-ray sensor is set to the length for cephalometric imaging, and a part of the area is used for panoramic imaging. In this structure, data may be read only from the area used for panoramic imaging, and data may be read from the entire area on cephalometric imaging.

The frame rate may be changed during imaging in an imaging mode. An example is explained with reference to FIGS. 31(a) and (b).

Figure 31:
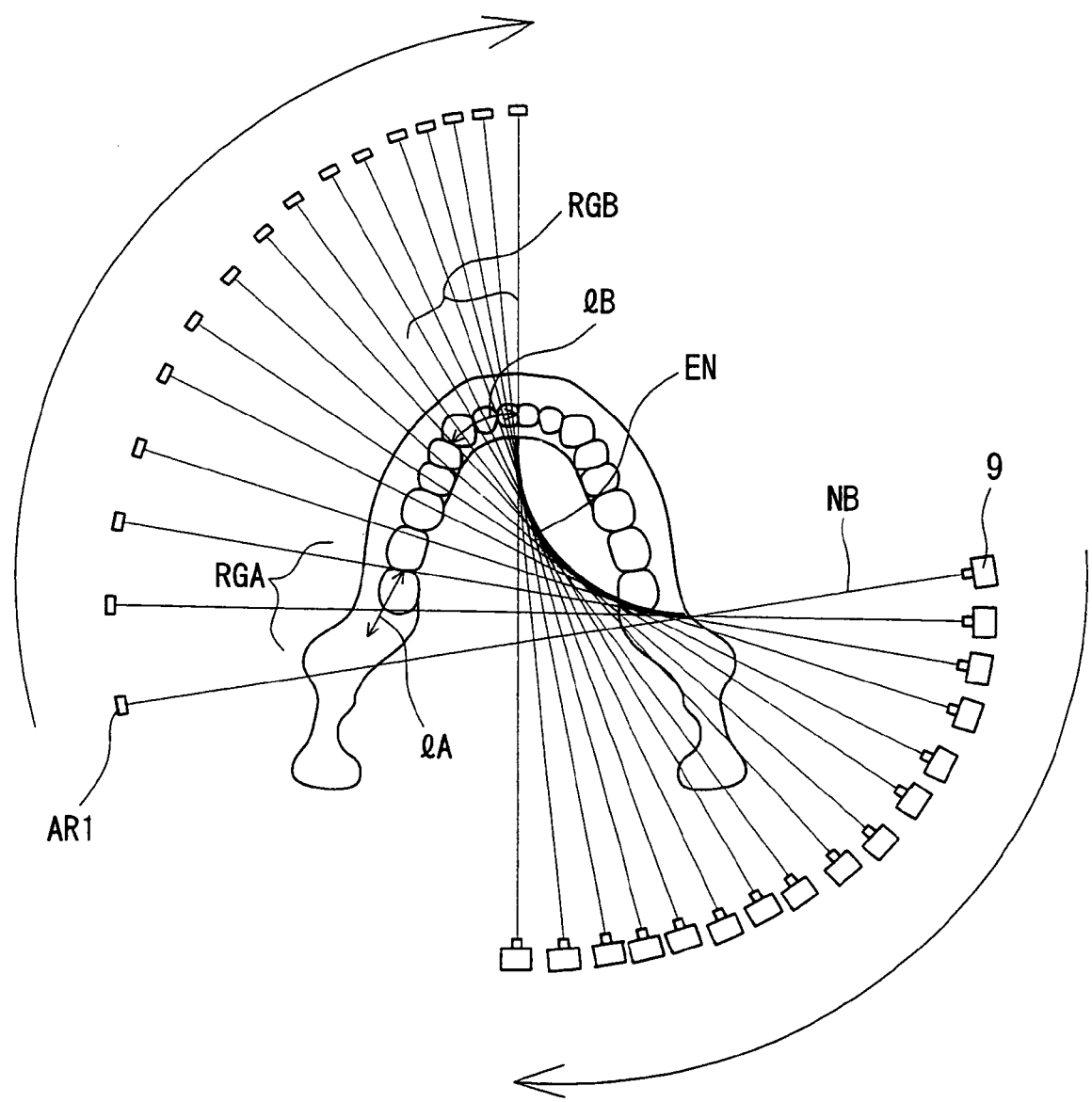
FIG. 31 is a diagram on a change in radiation direction of a narrow beam NB for each unit time.

The panoramic X-ray imaging wherein an X-ray beam follows an envelope EN is already explained with reference to FIG. 21. FIG. 31(a) also shows a situation of panoramic imaging where the long and narrow beam NB has envelope lines EN, similarly to FIG. 21. In FIG. 31(a), the change in irradiation direction of the long and narrow beam NB per unit time is illustrated. In the panoramic imaging on the dental arch where the long and narrow beam NB has the envelope lines EN when the rotation speed or the angular speed of the rotary arm (supporter) 4 rotating around the rotary shaft 4a is constant, the change in angle of irradiation direction per unit time is sharp around cheek teeth as shown as area RGA than that in the front teeth, or the change in angle of irradiation direction per unit time is slow around front teeth as shown as area RGB than that in the cheek tooth.

The change in angle of irradiation direction per unit time around area RGB may become about three times that in the area RGA. Therefore, if the frame rate is constant, the number of images to be read or the number of frame in the region to be imaged is smaller in the region RGA and larger in the region RGB. It is assumed that IA denotes the length along the dental arch in the region RGA and IB denotes the length along the dental arch in the region RGB, and that $\alpha$ denotes the number of frames in the region RGA and $\beta$ denotes the number of frames in the region RGB. If the length IA is equal to IB, $\alpha<\beta$. That is, as to the number of frames, the frames acquired in the length IA in the region RGA are sparser, and the frames acquired in the length IB in the region RGB are denser.

In the range RGA, if the frame rate is increased, the number of frames acquired in the range RGA can be increased, so as to compensate the sparser number of frames in the range RGA. For example, the frame rate can be adjusted so that $\alpha=\beta$.

It is explained above that the frame rate is increased so as to compensate the sparser number of frames. However, the frame rate may be increased positively in order to take details of an image of a portion sharply. In X-ray imaging such as panoramic imaging wherein the X-ray detector is moved relative to an object, if the frame rate is increased, the number of frames to be acquired in a particular region of a portion to be imaged is increased, as explained above. By using this fact, details can be reconstructed sharper by using many frames acquired at a higher frame rate. In the above-mentioned example, if the front teeth are wanted to be imaged sharper, the front teeth may be imaged at the higher frame rate.

In the example described above, the frame rate is adjusted to have an appropriate number of read-out images or frames relative to the portion to be imaged. However, the frame rate may be controlled in order to control the image density of read-out images or frames.

For example, when a portion to be imaged is deficient on hard tissue, the X-rays detected in the two-dimensional detection plane of the digital X-ray sensor 14 becomes excessive, and a phenomenon happens that portions exceeding the upper limit of detection of the digital X-ray sensor 14 have the same uniform density. On the other hand, when a portion to be imaged is abundant on hard tissue, the amount of X-rays to be detected in the two-dimensional detection plane 13e in the digital X-ray sensor 14 is deficient, and a phenomenon happens that portions exceeding the lower limit of detection of the digital X-ray sensor 14 are not displayed uniformly.

The frame rate may be controlled in order to adjust the degree of sufficiency. That is, if the detected X-rays are excessive, the frame rate is increased, and the times for reading the image are increased. Thus, the charges to be accumulated in the imaging elements until the image is read out can be decreased, and the phenomenon can be prevented that portions exceeding the upper limit of detection of the digital X-ray sensor 14 have the same uniform density. On the other hand, if the detected X-rays are deficient, the frame rate is decreased, and the times for reading the image are decreased. Thus, the phenomenon can be prevented that portions exceeding the lower limit of detection of the digital X-ray sensor 14 are not displayed uniformly.

In the panoramic imaging for dentistry, it is known that the X-rays detected in the two-dimensional detection plane 13e in the digital X-ray sensor 14 are insufficient around the front teeth in a range wherein the long and narrow beam NB transmits cervical vertebrae at the neck wherein the X-rays are absorbed. For example, the frame rate is decreased in the range as mentioned above so as to decrease the read-out times of image data.

In a software program used for the control by the CPU 19, for example, the amount of X-rays detected in the two-dimensional detection plane 13e is monitored always, and the frame rate is decreased automatically to control the generator 14a of sensor control signal when the detection level of the digital X-ray sensor 14 reaches a lower limit. On the contrary, in another software program, when the detection level of the digital X-ray sensor 14 becomes an upper limit, the frame rate is increased automatically to control the generator 14a of sensor control signal.

Because the X-rays detected in the two-dimensional detection plane 13e are obtained as digital data, the amount of X-rays can be presented easily as numerical values. The amount of X-rays detected in the two-dimensional detection plane 13e can be monitored by using all the imaging elements in the two-dimensional detection plane 13e. Alternatively, a part of the imaging elements on which X-rays are detected may be used.

Even when the frame rate is changed and the number of frames is increased or decreased, a smooth panoramic image can be obtained by adjusting the superposition of the acquired frames for accumulation at the same object sites as mentioned above.

As to the frame rate, its change pattern may be stored preliminarily in a storage device such as a hard disk. The storage device may be provided in the controller 29. For example, in the panoramic imaging mentioned above, a range where the narrow beam NB irradiates the cervical vertebrae is generally common though the range is different to some extent among persons to be imaged. Therefore, by assuming a standard model of a head obtained empirically on the distribution of bones, soft tissues and the like, a standard frame change pattern may be set and stored, and the frame rate is controlled according to the frame rate change pattern. In this case, if the pattern is prepared for various ages and sexes, the most appropriate change pattern can be selected according to a person to be imaged for suitable control.

Preferably, a generation pattern for the motor drive signal 20 for driving the motor for rotating the rotary arm 4 is stored in the storage device for each imaging, and a pattern for changing the frame rate is also stored based on the generation of motor drive signals according to the generation pattern. Then, the frame rate can be changed based on the patterns as the imaging progresses.

Preferably, a detector for detecting angle or angular speed such as a rotary encoder, an angle sensor or an angular speed sensor (sensors provided for detecting the movement of the supporter) may be attached to the rotary shaft 4a of the rotary arm (supporter) 4 in order to calculate at least one of rotary angle, rotary angular speed and rotary speed of the rotary arm 4 to change the frame rate. At the start of imaging, the image data is started to be read in the digital X-ray sensor 14, and the read-out is continued at a frame rate determined based on the at least one of rotary angle, rotary angular speed and rotary speed. When the imaging is completed, the read-out is completed.

In the above-mentioned panoramic imaging wherein the rotary shaft 4a itself is moved while the rotary arm (supporter) 4 is rotated, the loci of the X-ray source 9 and the digital X-ray sensor 14 under imaging in the two-dimensional detection plane 13e are calculated, and the speed of relative movement of the X-ray source 9 and the digital X-ray sensor 14 under imaging on panoramic sections in a dental arch is calculated. Then, the data are read at the frame rate determined preliminarily based on the calculated relative speed. In this case, the loci of the X-ray source 9 and the two dimensional detection plane 13e can be calculated based on at least one of the movements of the Y table 8j and the X table 8i in the XY table 8, and the rotation angle, the rotation angular angle and the rotation speed of the rotary arm 4.

In order to calculate the relative speed of the X-ray source 9 and the two-dimensional detection plane 13e during imaging on panoramic sections of the dental arch, a program for the calculation is stored in a storage device such as a hard disk (not shown) in the controller 29. The CPU 19 runs the program to calculate the relative speed based on at least one of the rotation angle, rotation angular speed, rotation speed of the rotary arm 4 detected with the sensors provided for detecting the movement of the supporter.

The position of panoramic sections in the dental arch can be set based on the coordinates of the panoramic sections in panoramic imaging. For example, it is known for panoramic imaging that the front teeth of the dental arch in a head to be imaged is positioned correctly by the object holder, and the coordinates of panoramic sections in the dental arch are set based on a general shape of dental arch and the positioned front teeth. Thus, the coordinates of the panoramic sections can be set based on the position of the front teeth obtained from the object holder. The general shape of dental arch is stored in the storage device, and the CPU 19 can set the coordinates of the panoramic sections of the dental arch. Alternatively, a person as an object bites a two-dimensional pressure sensor to detect correct two-dimensional coordinates of the panoramic sections of the dental arch.

As explained above on the panoramic imaging, the pattern for changing the frame rate can be stored preliminarily in the storage device according to the imaging type such as panoramic imaging and CT imaging and parameters therefor. In this case, as imaging is started, the digital X-ray sensor 14 starts to read image data. It continues to read image data according to the preliminarily determined pattern as the time passes. At the end of imaging, the read-out is stopped.

The above-mentioned sensors provided for detecting the movement of the supporter may be mounted to the rotary shaft 4a of the rotary arm (supporter) 4, and image data may be read at a frame rate in correspondence to the detected amount of movement of the rotary arm 4, without corresponding to the progress of time.

The frame rate may be set for each time. Alternatively, a standard frame rate is determined, for example 30 frames per second, and it may be multiplied with a coefficient according to the detected amount of movement of the rotary arm 4.

In panoramic imaging, the revolution of the rotary arm (supporter) 4 may be set to a lower speed in a range where the long and narrow beam NB irradiates cervical vertebrae. In this case, the dose is increased due to lower speed. The frame rate may not be changed, or it may be changed for adjustment.

The frame rate may be different among the first and second imaging modes in X-ray imaging. For example, when a panoramic image is used only for the above-mentioned scout view, a higher frame rate is used for CT imaging to obtain a larger number of frames per unit time, while a frame rate lower than that in the CT imaging is used in panoramic imaging to obtain a smaller number of frames per unit time. On the other hand, when a panoramic image is used not only for a scout view, but also for a high density image, a higher frame rate is used for panoramic imaging to obtain a larger number of frames per unit time, while a frame rate lower than that in the panoramic imaging is used in CT imaging to obtain a smaller number of frames per unit time.

When the frame rate can be changed during imaging in one or both of the first and second imaging modes, the frame rate in the first imaging mode may become lower or higher than that in the second one during the imaging.

Examples of a combination of the first and second imaging modes are explained above. In any example, the frame rate in the first imaging mode can be set higher than that in the second one, or the frame rate in the second imaging mode can be set higher than that in the first one.

The invention claimed is:

1. A medical digital X-ray imaging apparatus having a plurality of imaging modes including computed tomography mode comprising:
    an X-ray source for generating X-rays;
    a digital X-ray sensor having a two-dimensional detection plane for detecting the X-rays;
    a supporter which supports the X-ray source and the digital X-ray sensor while interposing an object between the X-ray source and the digital X-ray sensor;

an image reconstructor which acquires data from the digital X-ray sensor and reconstructs an image based on the acquired data;
a mode selector for selecting one of a first imaging mode and a second imaging mode, the first imaging mode being CT imaging mode, the second imaging mode being panoramic imaging mode;
an irradiation field setter which sets an irradiation field of the X-rays according to the mode selected by said mode selector; and
wherein when the first imaging mode is selected, a first irradiation field is set by said irradiation field setter, and a first area in the two-dimensional detection plane of the digital X-ray sensor from which image data are read is set, in correspondence to the first imaging mode selected by said mode selector, while when the second imaging mode is selected, a second irradiation field different from the first irradiation field is set by said irradiation field setter, and a second area smaller than the first area in the two-dimensional detection plane of the digital X-ray sensor from which image data are read is set, in correspondence to the second imaging mode selected by said mode selector, while the same two-dimensional detection plane of the digital X-ray sensor is used to detect X-rays in the first and second imaging modes, and the first area can be shifted in the two-dimensional detection plane of the digital X-ray sensor in a direction parallel to an axial direction of a rotary shaft of said supporter for rotating the X-ray source and the digital X-ray sensor around the object.

2. The medical digital X-ray imaging apparatus according to claim 1, wherein the irradiation field in the first imaging mode is smaller than that in the second imaging mode.

3. The medical digital X-ray imaging apparatus according to claim 2, wherein in the digital X-ray sensor a time for acquiring the image data in an imaging area of the object in the second imaging mode is shorter than that in the first imaging mode.

4. The medical digital X-ray imaging apparatus according to claim 3, or 2, further comprising a combiner which combines signals of adjacent imaging elements to be dealt as a pixel.

5. The medical digital X-ray imaging apparatus according to claim 1, wherein frame rate can be changed during imaging in the second imaging mode.

6. The medical digital X-ray imaging apparatus according to claim 5, wherein the frame rate is changed during imaging based on detection of a dose of the X-rays received by the digital X-ray sensor, or the frame rate is changed during imaging according to a predetermined change pattern.

7. The medical digital X-ray imaging apparatus according to claim 1, wherein the first area in the two-dimensional detection plane of said digital X-ray sensor is selected among a plurality of areas of different sizes.

8. A medical digital X-ray sensor having a two-dimensional detection plane for detecting X-rays transmitting an object in a plurality of imaging modes including computed tomography scanning, wherein an area in the two-dimensional detection plane from which image data are read is changed according to selection of a mode among first and second imaging modes, the first imaging mode being CT imaging mode, the second imaging mode being panoramic imaging mode, and an irradiation field of the X-rays irradiated on the two-dimensional detection plane is set according to the selected mode, and an irradiation field in the second imaging mode is different from that in the first imaging mode, while the same two-dimensional detection plane of the digital X-ray sensor is used to detect X-rays both in the first and second imaging modes, and a first area in the two-dimensional detection plane of the digital X-ray sensor from which image data are read, in correspondence to the selected first imaging mode, can be shifted in the two-dimensional detection plane of the digital X-ray sensor in a direction parallel to an axial direction of a rotary shaft of a supporter for rotating an X-ray source and the digital X-ray sensor around an object.

9. A medical digital X-ray imaging apparatus having a plurality of imaging modes including computed tomography mode comprising:
an X-ray source for generating X-rays;
a digital X-ray sensor having a two-dimensional detection plane for detecting the X-rays;
a supporter which supports the X-ray source and the digital X-ray sensor while interposing an object between the X-ray source and the digital X-ray sensor;
an image reconstructor which acquires data from the digital X-ray sensor and recontructs an image based on the acquired data;
a mode selector for selecting one of a first imaging mode and a second imaging mode, the first imaging mode being CT imaging mode, the second imaging mode being panoramic imaging mode;
an irradiation field setter which sets an irradiation field of the X-rays according to the mode selected by said mode selector,
wherein when the first imaging mode is selected, a first irradiation field is set by said irradiation field setter, the first irradiation field can be shifted by the irradiation field setter in a direction parallel to an axial direction of a rotary shaft in said supporter for rotating the X-ray source and the digital X-ray sensor around the object, and a first area in the two-dimensional detection plane of the digital X-ray sensor from which image data are read is set, in correspondence to the first imaging mode selected by said mode selector, while when the second imaging mode is selected, a second irradiation field different from the first irradiation field is set by said irradiation field setter, and a second area smaller than the first area in the two-dimensional detection plane of the digital X-ray sensor from which image data are read is set, in correspondence to the second imaging mode selected by said mode selector, while the same two-dimensional detection plane of the digital X-ray imaging sensor is used to detect X-rays in the first and second imaging modes.

10. The medical digital X-ray imaging apparatus according to claim 9, wherein the first area in the two-dimensional detection plane of said digital X-ray sensor is selected among a plurality of areas of different sizes.

* * * * *